United States Patent
Takagi et al.

(10) Patent No.: US 7,189,751 B2
(45) Date of Patent: Mar. 13, 2007

(54) OXA(THIA)ZOLIDINE COMPOUNDS, PROCESS FOR PREPARATION THEREOF AND ANTI-INFLAMMATORY AGENTS

(75) Inventors: Masae Takagi, Kanagawa (JP); Tadayuki Nishibe, Kanagawa (JP); Keiichi Ishimitsu, Kanagawa (JP)

(73) Assignee: Nippon Soda Co., Ltd., Tokyo (JP)

( * ) Notice: Subject to any disclaimer, the term of this patent is extended or adjusted under 35 U.S.C. 154(b) by 316 days.

(21) Appl. No.: 10/482,231

(22) PCT Filed: Jun. 25, 2002

(86) PCT No.: PCT/JP02/06324

§ 371 (c)(1),
(2), (4) Date: Dec. 19, 2003

(87) PCT Pub. No.: WO03/000668

PCT Pub. Date: Jan. 3, 2003

(65) Prior Publication Data
US 2004/0186096 A1    Sep. 23, 2004

(30) Foreign Application Priority Data
Jun. 25, 2001    (JP)    ............................. 2001-191391

(51) Int. Cl.
*A61K 31/42*    (2006.01)
*C07D 263/02*    (2006.01)
(52) U.S. Cl. ..................................... 514/374; 548/215
(58) Field of Classification Search ................ 548/215; 514/374
See application file for complete search history.

(56) References Cited

U.S. PATENT DOCUMENTS

| | | | |
|---|---|---|---|
| 4,290,870 A | 9/1981 | Kondoh et al. | |
| 5,198,454 A | 3/1993 | Chiou | |
| 5,955,616 A | 9/1999 | Ohtani et al. | |
| 6,762,200 B2 * | 7/2004 | Takagi et al. | 514/377 |
| 2004/0220244 A1 * | 11/2004 | Takagi et al. | 514/365 |

FOREIGN PATENT DOCUMENTS

| | | |
|---|---|---|
| EP | 0 081 584 A1 | 6/1983 |
| GB | 2023857 | 1/1980 |
| JP | 53-152091 | 11/1979 |
| WO | WO 00/42031 | 7/2000 |
| WO | WO 01/72723 | * 10/2001 |

OTHER PUBLICATIONS

Hosomi et al., J. of Organic Chemistry, 1990, 55(19):5308-5310.*
JP Pat. Application KOKAI publication No. 63-41470.
JP Pat. Application KOKAI publication No. 63-41471.
Tetrahedron Lett., 32(42), pp. 5987 to 5990, (1991).
Irvine, R., Biochemical Journal 204: 3-16 (1982).
Glaser, K.B., Advances in Pharmacology 32: 31-66 (1995).
Dennis, E. A., Trends in Biochemical Science, 22: 1-2 (1997).
Balsinde, J. et al, Annual Review of Pharmacology and Toxicology, 39: 175-189 (1999).
Uozumi, N. et al, Nature 390: 618-621 (1997).
Bonventre, J.V. et al, Nature 390: 622-625 (1997).
Nagase, Nature Immunology, 1:42-46 (2000).
Musser, J. Med. Chem., vol. 30, pp. 2087-2093 (1987).
J. Heterocycl. Chem., vol. 23, No. 3, pp. 701-704 (1986) [English Summary].
J. Org. Chem., vol. 55, No. 19, pp. 5308-5310 (1990).

* cited by examiner

*Primary Examiner*—Joseph K. McKane
*Assistant Examiner*—Robert Shiao
(74) *Attorney, Agent, or Firm*—Lahive & Cockfield, LLP; Anthony A. Laurentano

(57) ABSTRACT

The present invention provides medicinal compositions characterized by comprising as the active ingredient either a compound represented by a formula [I] or a pharmaceutically acceptable composite thereof;

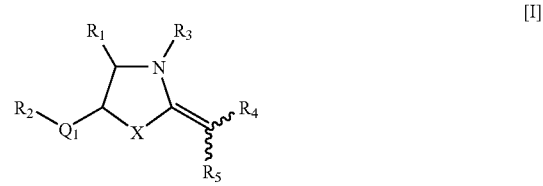

[wherein X represents oxygen or sulfur; $R_1$ represents e.g., $C_{1-4}$ alkyl, phenyl optionally substituted, etc.; $Q_1$ represents spacer consisted of 0 to 3 carbon atoms; $R_2$ represents, e.g., phenyl optionally substituted; $R_3$ represents, e.g., hydrogen, $C_{1-4}$ alkyl, or a group represented by the following formulae; —CONH—$R_6$; $R_4$ and $R_5$ represent e.g., nitro, cyano, $C_{1-4}$ alkylcarbonyl, respectively];
in particular, medicine which is useful as therapeutic and/or protective drugs for inflammatory diseases and/or allergic diseases by improving sick conditions accompanied with the stimulated phospholipase A(2) activity.

3 Claims, No Drawings

OXA(THIA)ZOLIDINE COMPOUNDS, PROCESS FOR PREPARATION THEREOF AND ANTI-INFLAMMATORY AGENTS

FIELD OF THE INVENTION

The present invention relates to novel compounds, process for preparation thereof, and medicinal compositions containing the active ingredient thereof, in particular, medicine comprising as the active ingredient either oxa(thia)zolidine compounds with phospholipase A(2) (hereinafter referred to as PLA(2)) inhibiting activity, or the pharmaceutically acceptable composites thereof.

BACKGROUND OF THE INVENTION

Inflammation is a series of defensive response process caused in the tissues, induced by the applied injurious events (inflammatory stimuli) on any parts of a human body. When the tissues are damaged by inflammatory stimuli that could be caused by bacterial infections, immunological responses or physical injuries, the tissues respond (acute inflammation) to the stimuli, followed by excluding the stimuli to repair the damages. Alternatively, if the exclusion is difficult, the damages are progressed to induce continuously tissue swelling (chronic inflammation). Those inflammatory responses are well known to be associated with several diseases, and various mediators are known to be associated with each step during the inflammation process, constituted with activation of various cells and interactions with each other.

PLA(2) is a diverse class of enzymes, catalyzing preferentially the hydrolysis of the sn-2 acyl-ester of glycerophospholipids, that are major components of cell membranes, to liberate fatty acids. It is also well known that the PLA(2)s are responsible for deacylation-reacylation process required for cell membrane repair and maintenance, and the hydrolyzed products, as well as the further metabolites, are lipid mediators with strong diverse physiological activities. The liberated product, arachidonic acid with some activity as mediator, is further metabolized in respective inflammation-associated cells to prostaglandins, thromboxanes, lipoxins, leukotrienes, etc., which induce characteristic physiological responses, respectively (Irvine, R., *Biochemical Journal* 204: 3–16 (1982).). The other product, lysophosphatidylcholine not only plays roles as mediator, but also is utilized as a precursor of platelet activating factor (hereinafter referred to as PAF). These lipid mediators play an essential role to maintain homeostasis of living organisms, however, when they produced to excessive amounts under sick conditions associated with inflammation, they could cause adversely effects. In fact, steroidal anti-inflammatory drugs and various non-steroidal anti-inflammatory drugs (hereinafter referred to as NSAIDs) are known to interfere with the eicosanoid cascade, have been widely used in clinical therapy. As PLA(2) is positioned at the upstream of the eicosanoid cascade and is believed to be the rate-limiting step in the generation of these lipid mediators, this enzyme has been expected to be the promising target for research and development of novel anti-inflammatory drugs (Glaser, K. B., *Advances in Pharmacology* 32: 31–66 (1995).).

Recently, numerous PLA(2)s have been identified and rapidly become a large superfamily consisted of more than 15 isozymes are subdivided into four groups, on the basis of the protein structures and the characteristics in the enzymatic activities(Dennis, E. A., *Trends in Biochemical Science*, 22: 1–2 (1997), and Balsinde, J. et al, *Annual Review of Pharmacology and Toxicology*, 39: 175–189 (1999), etc.).

Among them, it is noted that only the particular isozymes are shown high specificity against arachidonyl-phospholipids, as well as the enzymatic activity of the particular isozymes are selectively enhanced in a case of inflammatory disorder. As the examples for such inflammation-associated PLA(2)s, group IV-cytosolic PLA(2) (hereinafter referred to as IV-cPLA(2); molecularweight 85 kDa) and the subtypes IIA, IID, V and X of secretory PLA(2) (hereinafter referred to as sPLA(2); molecular weight 14 kDa) may be exemplified. Among these, IV-cPLA(2) is particularly considered as the responsible isozyme for producing the lipid mediators in the inflammatory diseases, which is supported by findings from the 'knockout' (IV-cPLA(2)$^{-/-}$)mice (Uozumi, N. et al, *Nature* 390: 619–622 (1997), Bonventre, J. V. et al, *Nature* 390: 622–625 (1997), and Nagase, T. et al, Nature Immunology1: 42–46 (2000).). Therefore, the enhanced lipid mediators production under sick conditions could be suppressed by inhibiting IV-cPLA(2) activity, thereby facilitating remedy and/or prevention of the inflammatory diseases. Such diseases can be exemplified as following: anaphylaxis induced by various inflammatory stimuli, septic shock, fever and pain; respiratory diseases, such as bronchitis, pneumonia, and adult respiratory distress syndrome; digestive diseases, such as inflammatory intestine disorder, Crohn's disease, ulcerative colitis, hepatitis, and nephritis; cardiovascular diseases, such as vasculitis and arteriosclerosis; allergic inflammatory diseases, such as rhinitis, asthma and atopic syndromes; and auto-immune diseases such as rheumatism; ischemia/reperfusion injuries, such as cerebral infarction and myocardial infarction; nerve degenerative diseases, solar keratosis, psoriasis, and the like.

However, as no drug has been developed yet, which shows remedial effects in the clinical therapies by inhibiting the enzyme activity, it is desired to develop such a new drug that can specifically and comprehensively control the lipid mediators production in inflammatory diseases, with excellent therapeutic and preventive effects.

In WO97/05135, as oxa(thia)zolidine compounds having activity of inhibiting the PLA(2) activity, the compounds represented by the following formula are disclosed.

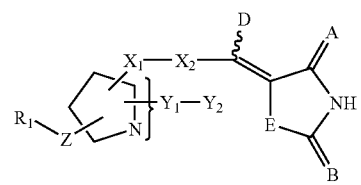

In addition, 2-imino-4-oxothiazolidine compounds represented by the following chemical formula is disclosed in WO93/10789.

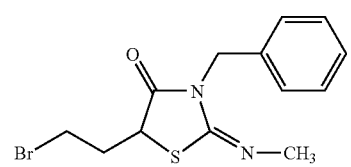

Furthermore, it is described in Musser, J. H., et al, *Journal of Medicinal Chemistry* 30: 2097–2093(1987). and GB 2183641 that the compounds represented by the following chemical formula show anti-inflammatory activities, etc. by Leukotriene $D_4$ antagonistic effects.

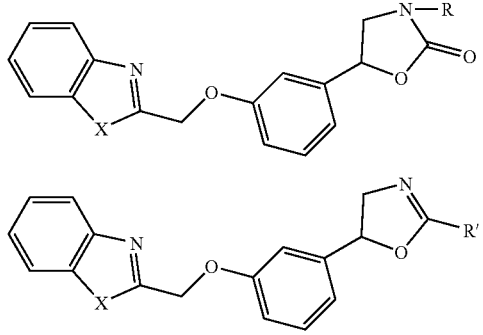

As for oxazolidine compounds relevant to this invention, (4-methyl-5-phenyl-2-oxazolidinylidene)-propane dinitrile and the process for preparation thereof are disclosed in Huche, M. & Lhommet, G., *Journal of Heterocyclic Chemistry* 23 (3): 701–4(1986).

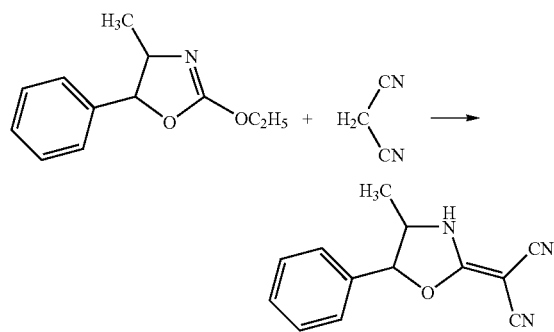

In addition, the compounds represented by the following chemical formula are disclosed in the catalogue for manufactured goods dealt by ChemDiv, Inc. or ChemStar, Ltd.

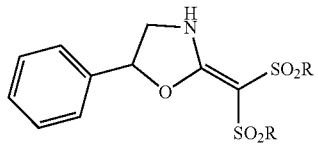

(wherein R represents ethyl or n-propyl)

Furthermore, the compounds represented by the following chemical formula and the process for preparation thereof are disclosed in Hosomi, A., et al, *Journal of Organic Chemistry* 55: 5308–5310(1990).

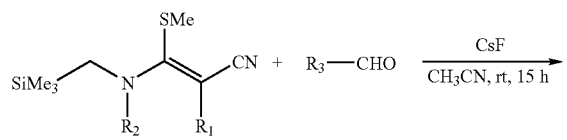

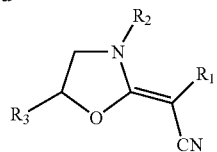

(wherein R1, R2 OR R3 represents hydrogen, methyl, ethyl or benzyl)

As for thiazolidine compounds relevant to this invention, the compounds represented by following chemical formula and the use for photo-polymerization initiator thereof are disclosed in Jpn. Pat. Appln. KOKAI publication No. Sho 53-152091.

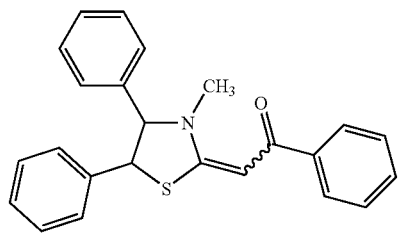

However, it has not been known so far that those oxa(thia)zolidine compounds have PLA(2) inhibitory activity or anti-inflammatory activity.

DISCLOSURE OF THE INVENTION

As described above, it is understood that the enhanced PLA(2) activity plays a major role in the progress of various inflammatory diseases. Therefore, an object of the present invention is to provide medicinal compositions, which is effective to remedy the inflammatory sick condition and to cure or prevent the relevant disease, and novel compounds to be used for the medicinal composition.

As a result of the studies by the inventors of the present invention for aiming at achieving the aforementioned object, the oxa(thia)zolidine compounds, which had been known to have acaricidal activity, have been found out also having inhibitory activity on PLA(2), thereby reaching the present invention.

The present invention is constituted with the following aspects (1) through (17).

(1) A medicinal composition characterized by comprising as the active ingredient either a compound represented by a formula [I] or a pharmaceutically acceptable composite thereof;

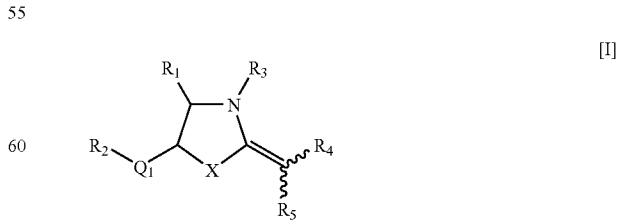

[wherein X represents oxygen or sulfur,
$Q_1$ represents —$(CH_2)_n$— or —CH=CH— (n represents 0, or an integer ranging from 1 to 3), $R_1$ represents hydrogen, $C_{1-6}$ alkyl, $C_{1-6}$ haloalkyl, phenyl (optionally substituted by $A_1$)—$C_{1-6}$ alkyl or phenyl optionally substituted by $A_1$, $R_2$ represents phenyl optionally substituted by $A_1$, naphthyl optionally substituted by $A_1$, indanyl optionally substituted by $A_1$, 1,2,3,4-tetrahydronaphthyl optionally substituted by $A_1$, 5 to 7-membered heterocyclic group optionally substituted by $A_4$ containing at least one heteroatom selected from a group consisting of oxygen, sulfur and nitrogen, $R_3$ represents hydrogen, $C_{1-6}$ alkyl optionally substituted by $A_2$, $C_{2-6}$ alkenyl optionally substituted by $A_2$, $C_{2-6}$ alkynyl optionally substituted by $A_2$, $C_{1-6}$ alkylcarbonyl optionally substituted by $A_2$, $C_{2-6}$ alkenylcarbonyl optionally substituted by $A_2$, $C_{1-6}$ alkoxycarbonyl optionally substituted by $A_2$, $C_{2-6}$ alkenyloxycarbonyl optionally substituted by $A_2$, $C_{1-6}$ alkylsulfonyl optionally substituted by $A_2$, $C_{2-6}$ alkenylsulfonyl optionally substituted by $A_2$, benzoyl optionally substituted by $A_3$, phenylsulfonyl optionally substituted by $A_3$, or a group represented by the following formula;

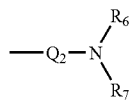

$C_{2-6}$ alkenyl optionally substituted by $A_2$, $C_{2-6}$ alkynyl optionally substituted by $A_2$, $C_{3-7}$ cycloalkyl optionally substituted by $A_4$, $C_{5-7}$ cycloalkenyl optionally substituted by $A_4$, $C_{1-6}$ alkylcarbonyl optionally substituted by $A_2$, $C_{1-6}$ alkylsulfonyl optionally substituted by $A_2$, phenyl optionally substituted by $A_3$, benzoyl optionally substituted by $A_3$, phenylsulfonyl optionally substituted by $A_3$, or 5 to 7-membered heterocyclic group optionally substituted by $A_4$ containing at least one heteroatom selected from a group consisting of oxygen, sulfur and nitrogen, m represents 1 or 2), $R_4$ represents hydrogen, cyano or a group represented by the following formula; -$Q_3$-$R_8$ (wherein $Q_3$ represents —CO— or —S(O)$_m$—, $R_8$ represents amino, $C_{1-6}$ alkyl optionally substituted by $A_2$, $C_{2-6}$ alkenyl optionally substituted by $A_2$, $C_{2-6}$ alkynyl optionally substituted by $A_2$, $C_{1-6}$ alkoxy optionally substituted by $A_2$, $C_{2-6}$ alkenyloxy optionally substituted by $A_2$, $C_{2-6}$ alkynyloxy optionally substituted by $A_2$, mono- or di-($C_{1-6}$ alkyl)amino optionally substituted by $A_2$, $C_{3-7}$ cycloalkyl optionally substituted by $A_4$, $C_{5-7}$ cycloalkenyl optionally substituted by $A_4$, phenyl optionally substituted by $A_3$, phenoxy optionally substituted by $A_3$, anilino optionally substituted by $A_3$, or 5 to 7-membered heterocyclic group optionally substituted by $A_4$ containing at least one heteroatom selected from a group consisting of oxygen, sulfur and nitrogen, m represents 1 or 2), $R_5$ represents nitro, cyano, or a group represented by the following formula; -$Q_3$-$R_8$ (wherein $Q_3$ and $R_8$ is same as defined in the above description), $A_1$ represents halogen, nitro, cyano, $C_{1-6}$ alkyl, $C_{2-6}$ alkenyl, $C_{1-6}$ haloalkyl, $C_{3-7}$ cycloalkyl, phenyl (optionally substituted by halogen, $C_{1-6}$ alkyl or $C_{1-6}$ haloalkyl), pyridyl, thienyl, $C_{1-6}$ alkoxy, methylenedioxy, $C_{1-6}$ alkylthio, $C_{1-6}$ alkylsulfenyl, $C_{1-6}$ alkylsulfonyl, mono- or di-($C_{1-6}$ alkyl) amino, $C_{1-6}$ haloalkoxy, benzyl, phenethyl, phenoxy, phenylthio, benzoyl, $C_{1-6}$ alkylcarbonyl, $C_{1-6}$ alkoxycarbonyl, $C_{1-6}$ haloalkylcarbonyl, $C_{1-6}$ haloalkoxycarbonyl, $C_{1-6}$ alkylcarbonyloxy, carbamoyl, or mono- or di-($C_{1-6}$ alkyl)carbamoyl, $A_2$ represents halogen, $C_{1-6}$ alkoxy, $C_{1-6}$ alkoxy $C_{1-6}$ alkoxy, amino, mono- or di-($C_{1-6}$ alkyl)amino, $C_{1-6}$ alkylcarbonyloxy, $C_{1-6}$ alkoxycarbonyl, mono- or di-($C_{1-6}$ alkyl) carbamoyl, mono- or di-($C_{1-6}$ alkyl)carbonylamino, morpholino, phenyl, or pyridyl optionally substituted by halogen, $A_3$ represents halogen, hydroxy, oxo, mercapto, nitro, amino, cyano, $C_{1-6}$ alkyl, $C_{1-6}$ haloalkyl, pyridyl, $C_{1-6}$ alkoxy, $C_{1-6}$ alkylthio, $C_{1-6}$ alkylsulfenyl, $C_{1-6}$ alkylsulfonyl, mono- or di-($C_{1-6}$ alkyl)amino, $C_{1-6}$ haloalkoxy, $C_{1-6}$ alkylcarbonyl, $C_{1-6}$ alkoxycarbonyl, carbamoyl, mono- or di-($C_{1-6}$ alkyl)carbamoyl, and $A_4$ represents halogen, hydroxy, oxo, $C_{1-6}$ alkyl, $C_{1-6}$ haloalkyl, $C_{1-6}$ alkoxy, $C_{1-6}$ alkylthio, $C_{1-6}$ alkoxy$C_{1-6}$ alkoxy, $C_{1-6}$ alkylcarbonyl, $C_{1-6}$ alkylsulfonyl, or $C_{1-6}$ alkoxycarbonyl.].

(2) Compounds represented by a formula [I'] or pharmaceutically acceptable composites thereof;

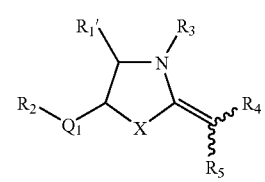

[1']

(wherein X, $Q_1$, $R_2$, $R_3$, $R_4$ and $R_5$ are same as defined in the section (1), $R_1$' represents $C_{1-6}$ alkyl, $C_{1-6}$ haloalkyl, phenyl(optionally substituted by $A_1$)—$C_{1-6}$ alkyl, or phenyl optionally substituted by $A_1$;

with an exception of the following compounds, provisory;

X represents sulfur, both $R_1$' and a group represented by $R_2$—$Q_1$ represent phenyl, $R_3$ represents methyl, $R_4$ represents hydrogen, $R_5$ represents benzoyl;

X represents oxygen, $R_1$' represents methyl, a group represented by $R_2$—$Q_1$ represents phenyl, $R_3$ represents hydrogen, both $R_4$ and $R_5$ represent cyano;

X represents oxygen, $R_1$' represents methyl, a group represented by $R_2$—$Q_1$ represents phenyl, $R_4$ represents hydrogen, $R_5$ represents nitro.).

(3) A process for preparation, characterized by the reaction bismethylthioethylene compounds represented by the following formula [II];

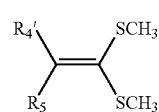

[II]

(wherein $R_5$ is same as defined in the section (1), $R_4$' is same as $R_4$ defined in the section (1) except for hydrogen), with 2-aminoethanol compounds represented by the following formula [III];

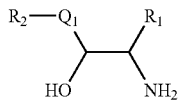

[III]

(wherein $R_1$, $R_2$, and $Q_1$ are same as defined as described above), to obtain oxazolidine compounds represented by a formula [I-1];

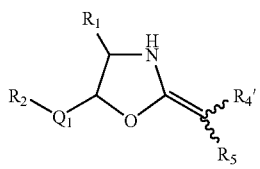

[I-1]

(wherein $R_1$, $R_2$, $R_5$, $R_4'$, and $Q_1$ are same as defined as described above)

(4) A process for preparation, characterized by the reaction 2-methylthio-2-thiazoline compounds represented by the following formula [IV];

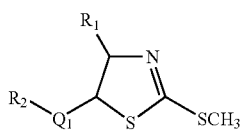

[IV]

(wherein $R_1$, $R_2$, and $Q_1$ are as defined in the section (1) described above), with active methylene compounds represented by the following formula [V];

(wherein $R_5$ is same as defined in the section (1), and $R_4'$ is same as defined in the section (3)), to obtain thiazolidine compounds represented by a formula [I-2];

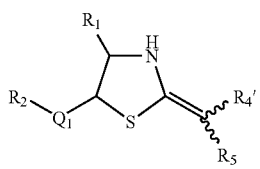

[I-2]

(wherein $R_1$, $R_2$, $R_4'$, $R_5$, and $Q_1$ are same as defined as described above).

(5) A process for preparation, characterized by the reaction oxa(thia)zolidine compounds represented by the following formula [I-3];

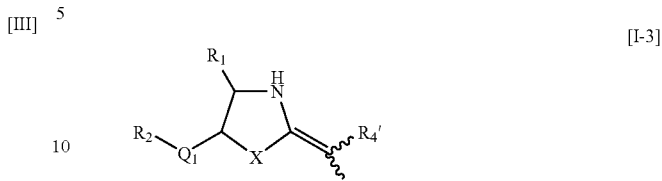

[I-3]

(wherein X, $R_1$, $R_2$, $R_4$, $R_5$, and $Q_1$ are same as defined in the section (1)), with halide compounds represented by the following formula [VI];

$R_3'$—Hal

[wherein $R_3'$ represents $C_{1-6}$ alkyl optionally substituted by $A_2$, $C_{2-6}$ alkenyl optionally substituted by $A_2$, $C_{2-6}$ alkynyl optionally substituted by $A_2$, $C_{1-6}$ alkylcarbonyl optionally substituted by $A_2$, $C_{2-6}$ alkenylcarbonyl optionally substituted by $A_2$, $C_{1-6}$ alkoxycarbonyl optionally substituted by $A_2$, $C_{2-6}$ alkenyloxycarbonyl optionally substituted by $A_2$, $C_{1-6}$ alkylsulfonyl optionally substituted by $A_2$, $C_{2-6}$ alkenylsulfonyl optionally substituted by $A_2$, benzoyl optionally substituted by $A_3$, phenylsulfonyl optionally substituted by $A_3$, or a group represented by the following formula;

—S(O)$_m$—NR$_6$R$_7$, (wherein $R_6$, $R_7$, and m are same as defined in the section (1)), Hal represents halogen], to obtain oxa(thia)zolidine compounds represented by a formula [I-4];

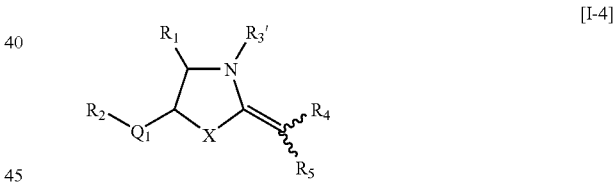

[I-4]

(wherein X, $R_1$, $R_2$, $R_4$, $R_5$, $Q_1$, and $R_3'$ are same as defined as described above).

(6) A process for preparation, characterized by the reaction oxa(thia)zolidine compounds represented by the following formula [I-3];

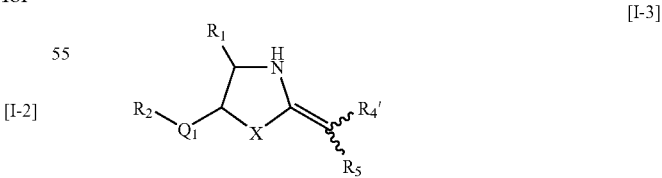

[I-3]

(wherein X, $R_1$, $R_2$, $R_4$, $R_5$, and $Q_1$ are same as defined in the section (1) described above), with compounds represented by the following formula [VII];

$R_7$NCZ (wherein $R_7$ is same as defined in the section (1),

Z represents oxygen or sulfur), to obtain oxa(thia)zolidine compounds represented by a formula [I-5];

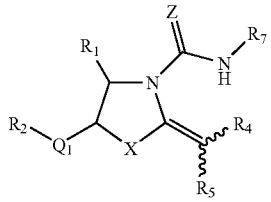

(wherein X, $R_1$, $R_2$, $R_4$, $R_5$, $R_7$, $Q_1$ and Z are same as defined as described above).

(7) A composition comprising as the active ingredient at least one selected from a group consisting of heterocyclic compounds represented by the formula [I] and the pharmaceutically acceptable composites thereof.

(8) An inhibitor of phospholipase A(2) activity comprising as the active ingredient at least one selected from a group consisting of heterocyclic compounds represented by the formula [I] and the pharmaceutically acceptable composites thereof.

(9) A use of a composition for a mammalian which requiring remedy for inflammatory diseases or disorders, where the composition is characterized by containing as the active ingredient at least one selected from a group consisting of heterocyclic compounds represented by the formula [I] and the pharmaceutically acceptable composites thereof.

(10) A method to remedy or reduce inflammatory diseases or disorders, curing and/or preventing taking turn for the worth by administering a medicinal composition, which is comprising an effective dose of at least one selected from a group consisting of compounds represented by the formula [I] and the pharmaceutically acceptable composites thereof to a mammalian requiring treatment.

(11) The method defined in the section (10); wherein the inflammatory diseases or the disorders are any of anaphylaxis, allergic inflammation, asthma, rhinitis, bronchitis, pneumonia, and adult respiratory distress syndrome, inflammatory intestine disorder, Crohn's disease, ulcerative colitis, ischemia/reperfusion injuries, vasculitis, arteriosclerosis, hepatitis, nephritis, nerve degenerative diseases, arthritis, dermatitis, solar keratosis, psoriasis, septic shock and fever.

(12) The method defined in the section (10), wherein the progress of the sick condition is due to inflammatory disease or disorder that is accompanied with the enhanced phospholipase A(2) activity.

(13) The method defined in the section (10), wherein the inflammatory disease or disorder is mediated by pro-inflammatory lipid mediators, such as arachidonic acid and the metabolites thereof, and/or lysophosphatidylcholines, and/ or platelet activating factor (PAF).

(14) The method defined in the section (10), wherein the pro-inflammatory lipid mediators are suppressed by the inhibitor of phospholipase A(2) activity.

(15) A use of a heterocyclic compound of the formula [I] for manufacturing of a medicinal composition, which is used for improving inflammatory and/or allergic sick condition and/or sick condition associated with immunity, and/or for the remedy of such diseases and disorders.

(16) A use of a composition as a medicine, where the composition contains as the active ingredient at least one selected from a group consisting of heterocyclic compounds represented by the formula [I] and the pharmaceutically acceptable composites thereof.

(17) A use of a composition as an anti-inflammatory drug, anti-allergic drug and/or immune controlling drug, where the composition contains as the active ingredient at least one selected from a group consisting of heterocyclic compounds represented by the formula [I] and the pharmaceutically acceptable composites thereof.

EMBODIMENTS FOR CARRYING OUT THE INVENTION

In the compounds according to the present invention, which are represented by the formula [I] described above,
the "halogen" denotes fluoro, chloro, bromo, and the like,
the "$C_{1-6}$ alkyl" denotes methyl, ethyl, propyl, iso-propyl, butyl, iso-butyl, sec-butyl and tert-butyl, and the like,
the "$C_{2-6}$ alkenyl" denotes vinyl, 1-propenyl, iso-propenyl, allyl, 2-butenyl, and the like,
the "$C_{2-6}$ alkynyl" denotes ethynyl, propynyl, butynyl, or an isomer thereof, and the like,
the "$C_{1-6}$ alkylcarbonyl" denotes acetyl, ethylcarbonyl, propylcarbonyl, iso-propylcarbonyl, butylcarbonyl, iso-butylcarbonyl, sec-butylcarbonyl, tert-butylcarbonyl, and the like,
the "$C_{1-6}$ alkoxycarbonyl" denotes methoxycarbonyl, ethoxycarbonyl, propoxycarbonyl, iso-propoxycarbonyl, butoxycarbonyl, iso-butoxycarbonyl, sec-butoxycarbonyl, tert-butoxycarbonyl, and the like,
the "$C_{2-6}$ alkenylcarbonyl" denotes ethenylcarbonyl, vinylcarbonyl, allylcarbonyl, and the like,
the "$C_{1-6}$ alkoxy" denotes methoxy, ethoxy, propoxy, iso-propoxy, butoxy, iso-butoxy, sec-butoxy, tert-butoxy, pentyloxy, hexyloxy, and the like,
the "$C_{2-6}$ alkenyloxy" denotes ethenyloxy, propenyloxy, allyloxy, hexenyloxy, and the like,
the "$C_{2-6}$ alkynyloxy" denotes acetynyloxy, propynyloxy, butynyloxy, hexynyloxy, and the like,
the "$C_{2-6}$ alkenyloxycarbonyl" denotes ethenyloxycarbonyl, propenyloxycarbonyl, allyloxycarbonyl, and the like,
the "$C_{1-6}$ haloalkyl" denotes chloromethyl, dichloroethyl, bromomethyl, trifluoromethyl, and the like,
the "$C_{1-6}$ alkylthio" denotes methylthio, ethylthio, propylthio, and the like, the "$C_{1-6}$ alkylsulfenyl" denotes methylsulfenyl, ethylsulfenyl, propylsulfenyl, and the like, and the "$C_{1-6}$ alkylsulfonyl" denotes methanesulfonyl, ethanesulfonyl, propylsulfonyl, iso-propylsulfonyl, butylsulfonyl, sec-butylsulfonyl, pentylsulfonyl, hexylsulfonyl, and the like,
the "$C_{2-6}$ alkenylsulfonyl" denotes ethenylsulfonyl, propenylsulfonyl, allylsulfonyl, and the like,
the "$C_{3-7}$ cycloalkyl" denotes cyclopropyl, cyclopentyl, cyclohexyl, cycloheptyl, and the like,
the "$C_{5-7}$ cycloalkenyl" denotes cyclopentenyl,
the "5- to 7-membered heterocyclic group" means a saturated or unsaturated heterocyclic group constituted by 5 to 7 atoms and containing at least one heteroatom selected from oxygen, sulfur and nitrogen, concretely, that includes tetrahydrofuranyl, tetrahydrothienyl, pyrrolidinyl, pyrazolidinyl, imidazolidinyl, tetrahydropyranyl, tetrahydrothiapyranyl, piperidinyl, pyrimidinyl, pyridyl, morpholino, and the like,
the "mono- or di-($C_{1-6}$ alkyl)amino" denotes methylamino, dimethylamino, ethylamino, methylethylamino, hexylamino, and the like,
the "mono- or di-($C_{1-6}$ alkyl)carbamoyl" denotes methylcarbamoyl, dimethylcarbamoyl, ethylcarbamoyl, methylethylcarbamoyl, and the like, the "mono- or di-($C_{1-6}$ alkyl)

carbonylamino" denotes acetylamino, diacetylamino, ethylcarbonylamino, acetylethylcarbonylamino, and the like, the "$C_{1-6}$ haloalkoxy" denotes chloromethoxy, dichloroethoxy, bromomethoxy, trifluoromethoxy, and the like, the "$C_{1-6}$ haloalkoxycarbonyl" denotes chloromethoxycarbonyl, dichloroethoxycarbonyl, bromomethoxycarbonyl, trifluoromethoxycarbonyl, and the like, the "$C_{1-6}$ alkylcarbonyloxy" denotes acetoxy, ethylcarbonyloxy, propylcarbonyloxy, butylcarbonyloxy, and the like, and the "$C_{1-6}$ alkoxy $C_{1-6}$ alkoxy" denotes methoxymethoxy, ethoxymethoxy, methoxyethoxy, and the like.

The "pharmaceutically acceptable composite" denotes a composite comprising the compound described above and an atoxic low-molecular compound those interact with ionic, hydrogen or coordinate bonds each other, at a particular combining ratio, and the compound should be liberated after the composite is solubilyzed in an aqueous solution. Specific examples for the pharmaceutically acceptable composite include salts with ionic materials such as hydrochlorides, organic acids, amino acids and the like, and solvates such as hydrates.

Now, the compounds represented by the formula [I] respectively include their structural isomers associated with at least the fourth and fifth positions of the oxa(thia)zolidine portion and their optical isomers. In addition, when $R_3$ in the compound is hydrogen, the following tautomers may be arisen.

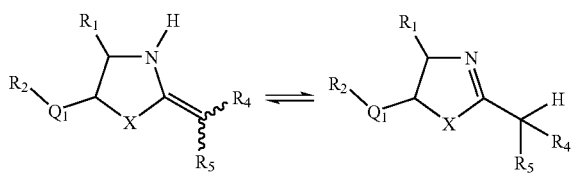

It is to be noted that each of the compounds according to the present invention is not limited to the specific isomers, namely compounds may include all possible isomers as well as possible racemic modifications. Furthermore, depending on circumstances, the compounds according to the present invention also may include the prodrugs and the metabolites of the compounds indicated above.

Now, the process for manufacturing the compounds according to the present invention is explained below.

Preparation Process 1:

The compounds represented by the formula [I-1], wherein X represents oxygen and $R_3$ represents hydrogen, may be prepared by the reaction bismethylthioethylene compounds [II] with 2-aminoethanol compounds [III], according to the following process;

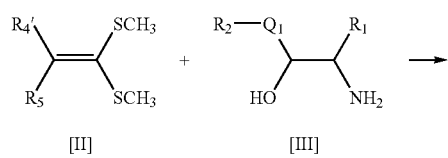

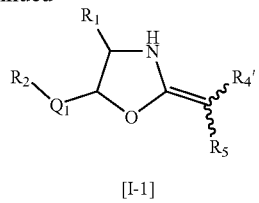

[I-1]

(wherein $R_1$, $R_2$, $R_4'$, $R_5$ and $Q_1$ are same as defined above.).

The reaction may be carried out in an organic solvent for 1 to several hours at the temperature ranging from room temperature to the boiling point of the used solvent. As the organic solvent for the above reaction, aromatic hydrocarbons such as benzene, toluene, xylene, and the like; alcohols such as methanol, ethanol, and the like; polar solvents such as DMF and DMSO; and the like may be used. Preferably, the above reaction is desired to be carried out in alcohols as solvent at about 100° C.

Preparation Process 2:

The compounds represented by the formula [I-2], wherein X represents sulfur, $R_3$ represents hydrogen and $R_4$ represents a substituent except for hydrogen, may be prepared by the reaction 2-methylthio-2-thiazoline compounds [IV] with active methylene compounds [V], according to the following process;

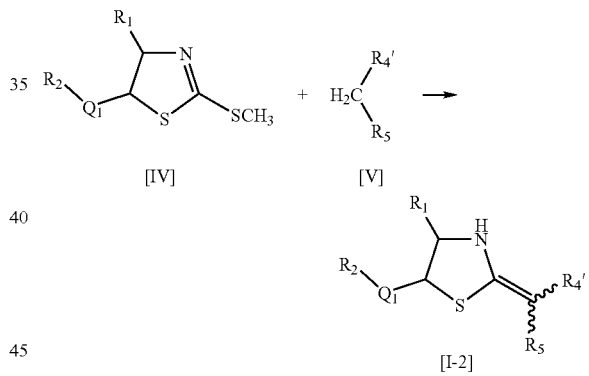

(wherein $R_1$, $R_2$, $R_4'$, $R_5$ and $Q_1$ are same as defined above.).

The above reaction may be carried out by heating with an acidic catalyst such as zinc chloride and the like, with or without solvents. Preferably, the above reaction is desired to be carried out by heating with zinc chloride as a catalyst at about 100° C. under nitrogen flow in an inert solvent such as benzene, toluene, DMF, and the like, when solvent is used.

The 2-methylthio-2-thiazoline compounds represented by the formula [IV] may be prepared according to the process described in Jpn. Pat. Appln. KOKAI Publication No. Sho 63-41471.

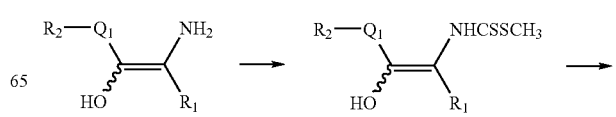

-continued

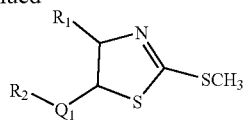

Preparation Process 3:

The compounds represented by the following formula, wherein $R_4$ represents hydrogen, may be prepared from the following formula [I-6] among of the compounds prepared according to either the preparation process 1 or the preparation process 2 as described above;

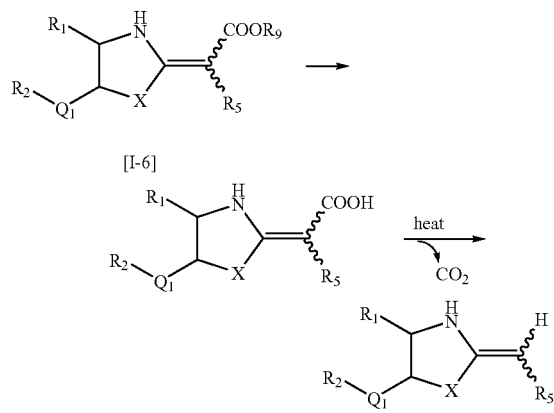

(wherein X, $R_1$, $R_2$, $R_5$ and $Q_1$ are same as defined above, $R_9$ represents $C_{1-6}$ alkyl.)

Preparation Process 4:

The compounds according to the present invention, wherein $R_3$ represents a substituent except for hydrogen, may be prepared by the reaction the following formula (I-3), which can be prepared according to either the preparation process 1, the preparation process 2 or the preparation process 3 as described above, with halide compounds (VI), or with either isocyanate compounds or isothiocyanate compounds represented by the formula (VII);

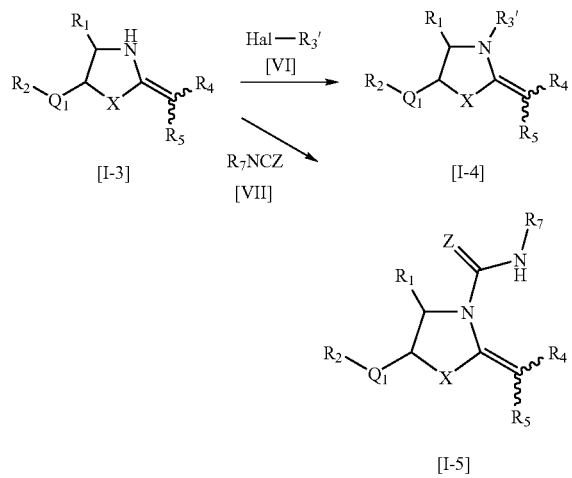

(wherein X, $R_1$, $R_2$, $R_3'$, $R_4$, $R_5$, $R_7$, Z, and $Q_1$ are same as defined above.).

The above reactions with halide compounds [VI] may be carried out in an organic solvent in the presence of a base for 1 to several hours at the temperature ranging from −20° C., to the boiling point of the used solvent, and preferably from 0° C. to 70° C. As the organic solvent for the reactions, DMF, THF, DMSO, alcohols and the like maybe used. As the base for the reactions, sodium hydride may be used, or any of alkoxides, triethylamine, 1,8-diazabicyclo(5,4,0)undecene-7 (hereinafter referred to as DBU) and the like may be used as well.

The reactions with either a cyanate or an isothiocyanate represented by a formula [VII] may be carried out in an organic solvent in the presence of a base for 1 to tens of hours at the temperature ranging from −20° C. to 60° C., and preferably from 0° C. to room temperature. As the organic solvent for the reactions, DMF, THF, chloroform, dioxane, benzene, and the like may be used. As the base for the reactions, triethylamine, DBU, Pyridine and the like may be used.

After each reaction represented above, work-up may be employed as conventionally to obtain the objective compound.

The chemical structures of the compounds according to the present invention were determined by means of MASS, NMR, etc.

<Anti-inflammatory Agents>

The compound, represented by the formula [I] or the pharmaceutically acceptable composite thereof may be administrated to humans and animals either directly or together with common carriers for pharmaceutical formulations. For applying the composite, the administration route is not limited, and either route of systemic administration or topical application, i.e. non-systemic administration, maybe selected appropriately upon necessity. Examples of the drug form for medical treatment include pharmaceutical formulations for oral administration such as tablets, capsules, granules, and powders, drinkable solutions, troches and the like; and parenteral solutions or suspensions for intravenous injection, intramuscular injection, subcutaneous injection and the like. In addition, other administration routes, such as through rectum with suppositories, and through lung (through nose or inhalation through mouth) with aerosols, powder inhalants, etc. may be employed for applying the medicinal composition according to the present invention. As pharmaceutical formulations suitable for the topical application to penetrate the active ingredient into the inflammatory regions through skins and mucosae, solutions, liniments, creams, emulsions, ointments and pastes, as well as drops suitable for the treatment to eyes, ears and noses may be exemplified. There is no limit for the amount of the active ingredient to be applied, and therefore, the dose may be appropriately selected in a wide range depending upon the administration routes, the applied compounds, and the treated patients, namely to humans or animals. In order to exert the desired medicinal effectiveness, the compound of the present invention is preferably administrated at a daily dose of 0.01–100 mg per kg bodyweight, with or without dividing the dose into several times. For the pharmaceutical formulations, it is preferable to contain the active ingredient in unit dosage form at a dose of 0.01 to 1,000 mg.

The pharmaceutical formulations for oral administration comprising the compound according to the present invention, such as tablets, capsules, granules and drinkable solutions, may be prepared according to any of the conventional methods. More specifically, the tablets may be prepared by mixing the compound represented by the formula [I] or the pharmaceutically acceptable composite thereof with pharmaceutical fillers, such as starch, lactose, gelatin, magnesium stearate, talc, gum arabic, and the like, and forming into tablets. The capsules may be prepared by mixing the compound represented by the formula [I] or the pharmaceutically acceptable composite thereof with an inactive pharmaceutical filler or diluent, and then charged into capsules made of hard gelatin, soft capsules, or the like to. The medicated syrups and elixirs for oral administration may be prepared by mixing the compound represented by the formula [I] or the pharmaceutically acceptable composite thereof with a sweetener such as sucrose, an antiseptic such as Methylparaben and Propylparaben, a coloring agent, a flavor, and the like. Further, the parenteral pharmaceutical formulations of the compound of the present invention may be prepared according to any of the conventional processes. For example, a parenteral pharmaceutical formulation may be prepared by dissolving the compound represented by the formula [I] or the pharmaceutically acceptable composite thereof with a sterilized liquid carrier. As the liquid carrier, water or saline solution may be preferably used. In order to provide the solution with a desired transparency, stability and congeniality for the parenteral use, approximately 0.1 to 1,000 mg of the active ingredient may be dissolved in either water or an organic solvent, and further dissolved with polyethylene glycol having a molecular weight of 200 to 5,000. For the preparation of the solution, it is preferable that a lubricant, such as polyvinylpyrrolidone, polyvinyl alcohol, sodium carboxymethyl cellulose, and methyl cellulose, is incorporated therein. Furthermore, a bactericide such as benzyl alcohol, phenol and Thimerosal, and a fungicide may be incorporated into the solution, in addition, an osmotic pressure conditioner, such as sucrose and sodium chloride, a local anesthetic, a stabilizer, a buffer agent and the like may be incorporated into the solution upon necessity. More stable pharmaceutical formulation for parenteral use may be provided by removing moisture in the frozen preparation following to the filling, by means of freeze-drying technique known in the field. Accordingly, it is also possible to resolve the lyophilized powder thereof to prepare a pharmaceutical formulation just before the use.

Although the compounds represented by the formula [I] or the pharmaceutically acceptable composites thereof show to have strong inhibitory activity on the liberation of arachidonic acid during inflammatory reaction, they have very weak inhibitory activity on the enzymatic hydrolysis due to secretary group IB-PLA(2) of porcine pancreas (hereinafter referred to as IB-sPLA(2); molecular weight 14 kDa) when using a phospholipid, of which carbon in the oleic acid substituent at the second position being labeled with a radioactive isotope, as the substrate. From this reason, an advanced safety can be expected for the compounds represented by the formula [I] and the pharmaceutically acceptable composites thereof.

Since a part of the compounds of the present invention also have herbicidal, insecticidal, acaricidal and/or fungicidal activities as well, and they can be used as agrochemicals. In particular, an excellent performance can be expected, as a drug provided by the compounds which additionally have inhibitory activity against fungi that causes infectious diseases to mammals, such as pneumonia by an opportunistically fungus infection.

Among the compounds according to the present invention, the preferable thiazolidine tautomer is trans, as for structural isomers associated with the fourth and fifth positions of the oxa(thia)zolidine portion.

BEST MODE FOR CARRYING OUT THE INVENTION

Now, the present invention is further explained in detail with reference to the examples.

EXAMPLE 1

Preparation of Trans-5-(4-chlorophenyl)-4-methyl-2-(1-ethoxycarbonyl-1-nitromethylene)-thiazolidine

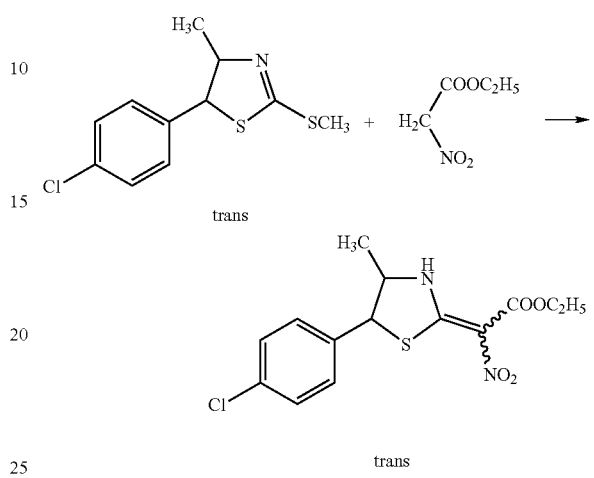

9 g of trans-5-(4-chlorophenyl)-4-methyl-2-methylthio-2-thiazoline, 4.7 g of ethyl nitroacetate, and 0.06 g of zinc chloride were added into a 100 ml capacity of four neck flask, and the mixture was heated under nitrogen flow at the temperature ranging from 110~130° C. for about five hours. After the completion of the reaction, the product mixture was dissolved with chloroform, washed with water, dried with magnesium sulfate, and then condensed under reduced pressure. The oily product obtained was purified by column chromatography to give 7.6 g of the title compound.

EXAMPLE 2

Preparation of Cis-5-(4-chlorophenyl)-4-methyl-2-(1-(4-methylphenylsulfonyl)-1-cyanomethylene)-oxazolidine

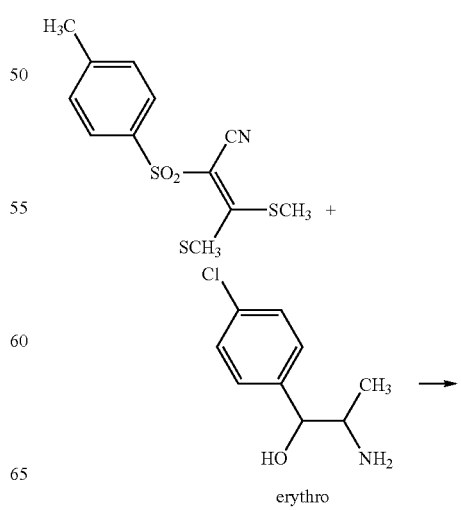

-continued

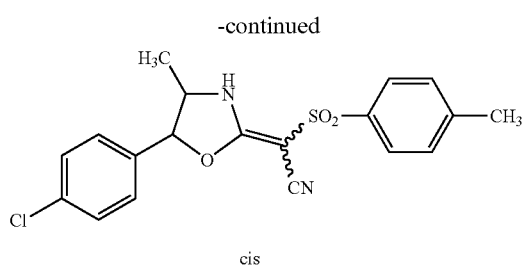

cis 1.5 g of 1-cyano-2,2-bismethylthio-1-(4-methylphenyl-sulfonyl)-ethylene and 0.93 g of erythro-α-(1-aminoethyl)-4-chlorobenzyl alcohol were added into 20 ml of methanol and the mixture was refluxed for 3 hours. After the completion of the reaction, the reaction solution was condensed under reduced pressure. The product obtained was purified by column chromatography to give 1.1 g of the title compound.

The representative compounds usable in the present invention including the compounds prepared in the Examples described above are presented in Tables 1 and 2. The abbreviations and the reference symbols in the tables have the following meanings, respectively.

Me: methyl, Et: ethyl, Pr: propyl, Hex: hexyl, Hep: heptyl, Allyl: allyl, Ac: acetyl, Naph: naphthyl, Ph: phenyl, Bn: benzyl, Bz: benzoyl, THP: tetrahydropyranyl, n: normal, c; cyclo.

TABLE 1

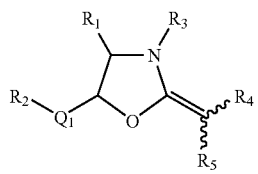

| Compound No. | $R_1$ | $Q_1$—$R_2$ | $R_3$ | $R_4$ | $R_5$ | $R_1$/ $Q_1$—$R_2$ | PhysicalConstant [ ]:MeltingPoint ° C. |
|---|---|---|---|---|---|---|---|
| 1-1 | H | Ph | Et | CN | CN | — | Oily substance |
| 1-2 | H | Ph | H | —COOMe | CN | — | [155] |
| 1-3 | H | Ph | H | —COOMe | $NO_2$ | — | |
| 1-4 | H | Ph | Me | CN | CN | — | [129] |
| 1-5 | H | Ph | Me | —COOMe | CN | — | [129] |
| 1-6 | H | 4-Cl—Ph | H | —COOEt | $NO_2$ | — | |
| 1-7 | H | 4-Cl—Ph | H | —COOMe | CN | — | [164.5] |
| 1-8 | H | 4-Cl—Ph | H | —$SO_2$Ph | CN | — | [254] |
| 1-9 | H | 4-Cl—Ph | Me | CN | CN | — | [209] |
| 1-10 | H | 2,6-diCl—Ph | H | CN | CN | — | [273] |
| 1-11 | H | 2,6-diCl—Ph | H | —$CONH_2$ | CN | — | [288] |
| 1-12 | H | 2,6-diCl—Ph | H | —COOEt | CN | — | [232] |
| 1-13 | H | 2,6-diCl—Ph | H | —COOMe | CN | — | [279] |
| 1-14 | H | 2,6-diCl—Ph | H | —$SO_2$Ph | CN | — | [188] |
| 1-15 | H | 2,6-diCl—Ph | Me | CN | CN | — | Oily substance |
| 1-16 | H | 2-MeO—Ph | Me | CN | CN | — | Oily substance |
| 1-17 | H | 4-CN—Ph | H | CN | CN | — | [234] |
| 1-18 | H | 4-Me—Ph | Me | CN | CN | — | Oily substance |
| 1-19 | H | 4-Ph—Ph | H | CN | CN | — | Oily substance |
| 1-20 | H | 4-Ph—Ph | H | —COOMe | CN | — | [201] |
| 1-21 | H | Bn | H | CN | CN | — | |
| 1-22 | H | Bn | H | —COOMe | CN | — | |
| 1-23 | H | Bn | H | —COOMe | $NO_2$ | — | |
| 1-24 | H | —CH=CH—Ph | H | —COOMe | CN | — | Oily substance |
| 1-25 | H | —CH=CH—Ph | H | CN | CN | — | |
| 1-26 | H | furfuryl | Me | —COOMe | CN | — | Oily substance |
| 1-27 | Me | methylenedioxyphenyl | H | —COOMe | $NO_2$ | | |
| 1-28 | Me | methylenedioxyphenyl | H | —COOMe | CN | | |
| 1-29 | Me | 4-(4-Me—Ph)—Ph | H | —COOEt | CN | | |
| 1-30 | Me | 4-AcO—Ph | H | —COOEt | $NO_2$ | | |

TABLE 1-continued

[Structure: oxazolidine ring with R1, R3 on top (N bears R3), R2-Q1 on left carbon, and =C(R4)(R5) exocyclic double bond]

| Compound No. | R$_1$ | Q$_1$—R$_2$ | R$_3$ | R$_4$ | R$_5$ | R$_1$/ Q$_1$—R$_2$ | PhysicalConstant [ ]:MeltingPoint ° C. |
|---|---|---|---|---|---|---|---|
| 1-31 | Me | 4-Ac—Ph | Bz | —COOEt | NO$_2$ | | |
| 1-32 | Me | 4-Allyl—Ph | H | —COOEt | NO$_2$ | | |
| 1-33 | Me | 4-Br—Ph | H | —SO$_2$-(4-Cl—Ph) | NO$_2$ | | |
| 1-34 | Me | 4-CF$_3$CO—Ph | H | —COOEt | NO$_2$ | | |
| 1-35 | Me | 4-CF$_3$—Ph | Ac | —COOEt | CN | | |
| 1-36 | Me | 4-CH$_2$Cl—Ph | 3-MeOCH2O-Bn | —COOEt | NO$_2$ | | |
| 1-37 | Me | 4-Cl—Ph | H | —COAllyl | —COAllyl | | |
| 1-38 | Me | 4-Cl—Ph | H | —COOEt | NO$_2$ | | |
| 1-39 | Me | 4-Cl—Ph | H | H | NO$_2$ | | |
| 1-40 | Me | 4-Cl—Ph | H | CN | CN | | |
| 1-41 | Me | 4-Cl—Ph | H | —SO$_2$-(4-Me—Ph) | CN | CIS | Oily substance |
| 1-42 | Me | 4-Cl—Ph | H | —SO$_2$-(4-Me—Ph) | CN | TRANS | [205–207] |
| 1-43 | Me | 4-Cl—Ph | H | —COOEt | CN | | |
| 1-44 | Me | 4-Cl—Ph | Et | —COOEt | CN | | |
| 1-45 | Me | 4-Cl—Ph | Bn | —COOMe | —COOMe | | |
| 1-46 | Me | 4-Cl—Ph | Bn | —COOEt | CN | | |
| 1-47 | Me | 4-Cl—Ph | —SO$_2$Me | —COOEt | CN | | |
| 1-48 | Me | 4-Cl—Ph | —COEt | —COOEt | CN | | |
| 1-49 | Me | 4-Cl—Ph | —COCH$_2$Cl | —COOEt | CN | | |
| 1-50 | Me | 4-Cl—Ph | —SO$_2$Me | —COOEt | CN | | |
| 1-51 | Me | 4-Cl—Ph | Allyl | —COOEt | CN | | |
| 1-52 | Me | 4-Cl—Ph | Bz | —COOEt | CN | | |
| 1-53 | Me | 4-Cl—Ph | —COCH$_2$Cl | —COOEt | CN | | |
| 1-54 | Me | 4-Cl—Ph | —COOEt | —COOEt | CN | | |
| 1-55 | Me | 4-Cl—Ph | —SO$_2$Ph | —COOEt | CN | | |
| 1-56 | Me | 4-Cl—Ph | —SO$_2$NMe$_2$ | —COOEt | NO$_2$ | | |
| 1-57 | Me | 4-Cl—Ph | —CH$_2$C≡CH | H | NO$_2$ | | |
| 1-58 | Me | 4-Cl—Ph | —CONH-cHex | H | NO$_2$ | | |
| 1-59 | Me | 4-Cl—Ph | H | H | NO$_2$ | | |
| 1-60 | Me | 4-Me—Ph | H | —SO$_2$-(4-Me—Ph) | CN | | |
| 1-61 | Me | 4-Me—Ph | H | —SO$_2$-(4-Me—Ph) | CN | | |
| 1-62 | Me | 4-Et—Ph | H | —COOMe | —COOMe | | |
| 1-63 | Me | 4-MeOCO—Ph | H | —COOEt | NO$_2$ | | |
| 1-64 | Me | 4-Me—Ph | —CO-Allyl | CN | CN | | |
| 1-65 | Me | 4-Me—Ph | —COOEt | CN | CN | | |
| 1-66 | Me | 4-Me—Ph | —CONH-2-THP | CN | CN | | |
| 1-67 | Me | 4-Me—Ph | 4-MeO—Bz | CN | CN | | |
| 1-68 | Me | 4-Me—Ph | 3-MeSO$_2$—Bz | CN | CN | | |
| 1-69 | Me | 4-Me—Ph | Bn | —COOEt | CN | | |
| 1-70 | Me | 4-Me—Ph | Bz | CN | CN | | |
| 1-71 | Me | 4-Me—Ph | —CSNH-cHex | CN | CN | | |
| 1-72 | Me | 4-Me—Ph | H | —COOEt | CN | CIS | [135–137] |
| 1-73 | Me | 4-Me—Ph | —CH$_2$C≡CH | —COOEt | CN | | |
| 1-74 | Me | 4-Me—Ph | —CONH-cHex | —COOEt | NO$_2$ | | |
| 1-75 | Me | 4-Me—Ph | —CONH-cHep | —COOEt | CN | | |
| 1-76 | Me | 4-Me—Ph | —CON(—Me)-cHex | —COOEt | NO$_2$ | | |
| 1-77 | Me | 4-Me—Ph | —CONH-(3-MeO-cHex) | —COOEt | NO$_2$ | | |
| 1-78 | Me | 4-Me—Ph | —CONHCO-cHex | —COOEt | NO$_2$ | | |
| 1-79 | Me | 4-Me—Ph | —CONH—CH$_2$COOMe | —COOMe | NO$_2$ | | |
| 1-80 | Me | 4-Me—Ph | —CO-nPr | —SO$_2$-(4-MeO—Ph) | —SO$_2$—Ph | | |
| 1-81 | Me | 4-Me—Ph | —CONH-2-THP | —SO$_2$—Ph | NO$_2$ | | |
| 1-82 | Me | 4-Me—Ph | —CONH-2-Py | —SO$_2$—Ph | NO$_2$ | | |
| 1-83 | Me | 4-MeSO$_2$—Ph | H | —SO$_2$-(4-AcO—Ph) | NO$_2$ | | |
| 1-84 | Me | 4-n-Pr—Ph | H | —COOEt | NO$_2$ | | |
| 1-85 | Me | 4-Ph—O—Ph | H | —COOEt | CN | | |
| 1-86 | Me | 4-Ph—Ph | Ac | —COOEt | CN | | |
| 1-87 | Me | 4-Ph—S—Ph | H | —COOEt | CN | | |
| 1-88 | Me | Bn | H | CN | CN | | |
| 1-89 | Me | —C$_2$H$_4$—Ph | H | —CONHMe | —CONHMe | | |
| 1-90 | Me | —CH=CH—Ph | H | —CONHMe | —CONHMe | | |
| 1-91 | Me | Naph | H | —COOMe | —COOMe | | |

TABLE 1-continued

Structure:

$$\underset{R_2-Q_1}{\overset{R_1\ \ R_3}{\underset{\phantom{.}}{\bigg\langle}}}\!\!\!\overset{N}{\underset{O}{\bigg\rangle}}\!\!=\!\!{\sim}\!\!\underset{R_5}{\overset{R_4}{\phantom{|}}}$$

(oxazolidine ring: positions 4 (R1), N-3 (R3), C-2 =C(R4)(R5), C-5 (Q1-R2))

| Compound No. | R₁ | Q₁—R₂ | R₃ | R₄ | R₅ | R₁/Q₁—R₂ | PhysicalConstant [ ]:MeltingPoint °C. |
|---|---|---|---|---|---|---|---|
| 1-92 | Me | 6-methyl-1,2,3,4-tetrahydronaphthalen-2-yl | H | —SO₂—Ph | CN | | |
| 1-93 | Me | 5-methyl-2,3-dihydro-1H-inden-2-yl | H | —COOMe | CN | | |
| 1-94 | Me | 6-methyl-1,2,3,4-tetrahydronaphthalen-2-yl | H | —SO₂—Ph | CN | | |
| 1-95 | Me | 6-methyl-1,2,3,4-tetrahydronaphthalen-2-yl | H | —COOMe | CN | | |
| 1-96 | Me | —CH₂-(2-furyl) | Me | —COOMe | CN | | |
| 1-97 | Et | 4-Cl—Ph | H | —COOEt | NO₂ | | |
| 1-98 | Et | 4-Me—Ph | H | —COOEt | —COMe | | |
| 1-99 | Ph | 4-PhO—Ph | H | —COOEt | —COOEt | | |
| 1-100 | 4-Me—Ph | 4-Me—Ph | H | —COOEt | —COOEt | | |
| 1-101 | Bn | Ph | H | —SO₂—Ph | CN | | |
| 1-102 | —C₂H₄Cl | 4-Cl—Ph | H | —SO₂—Ph | —COOEt | | |
| 1-103 | —CH₂Cl | 4-Cl—Ph | H | —SO₂—Ph | —COOEt | | |
| 1-104 | —CH₂F | Ph | H | —COOEt | —COOEt | | |

TABLE 2

Structure:

$$\underset{R_2-Q_1}{\overset{R_1\ \ R_3}{\underset{\phantom{.}}{\bigg\langle}}}\!\!\!\overset{N}{\underset{S}{\bigg\rangle}}\!\!=\!\!{\sim}\!\!\underset{R_5}{\overset{R_4}{\phantom{|}}}$$

(thiazolidine ring analog)

| Compound No. | R₁ | Q₁—R₂ | R₃ | R₄ | R₅ | R₁/Q₁—R₂ | PhysicalConstant [ ]:MeltingPoint °C. |
|---|---|---|---|---|---|---|---|
| 2-1 | H | Ph | Et | CN | CN | — | |
| 2-2 | H | Ph | H | —COOMe | CN | — | |
| 2-3 | H | Ph | H | —COOMe | NO₂ | — | |
| 2-4 | H | Ph | Me | CN | CN | — | |
| 2-5 | H | Ph | Me | —COOMe | CN | — | |
| 2-6 | H | 4-Cl—Ph | H | —COOEt | NO₂ | — | |
| 2-7 | H | 4-Cl—Ph | H | —COOMe | CN | — | |
| 2-8 | H | 4-Cl—Ph | H | —SO₂Ph | CN | — | |
| 2-9 | H | 4-Cl—Ph | Me | CN | CN | — | |
| 2-10 | H | 2,6-diCl—Ph | H | CN | CN | — | |
| 2-11 | H | 2,6-diCl—Ph | H | —CONH₂ | CN | — | |
| 2-12 | H | 2,6-diCl—Ph | H | —COOEt | CN | — | |

TABLE 2-continued

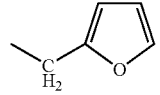

| Compound No. | $R_1$ | $Q_1$—$R_2$ | $R_3$ | $R_4$ | $R_5$ | $R_1$/ $Q_1$—$R_2$ | PhysicalConstant [ ]:MeltingPoint °C. |
|---|---|---|---|---|---|---|---|
| 2-13 | H | 2,6-diCl—Ph | H | —COOMe | CN | — | |
| 2-14 | H | 2,6-diCl—Ph | H | —SO$_2$Ph | CN | — | |
| 2-15 | H | 2,6-diCl—Ph | Me | CN | CN | — | |
| 2-16 | H | 2-MeO—Ph | Me | CN | CN | — | |
| 2-17 | H | 4-CN—Ph | H | CN | CN | — | |
| 2-18 | H | 4-Me—Ph | Me | CN | CN | — | |
| 2-19 | H | 4-NO$_2$—Ph | H | —COOMe | CN | — | |
| 2-20 | H | 4-NO$_2$—Ph | Me | —COOMe | CN | — | |
| 2-21 | H | 4-Ph—Ph | H | CN | CN | — | |
| 2-22 | H | 4-Ph—Ph | H | —COOMe | CN | — | |
| 2-23 | H | Bn | H | CN | CN | — | |
| 2-24 | H | Bn | H | —COOMe | CN | — | |
| 2-25 | H | Bn | H | —COOMe | NO$_2$ | — | |
| 2-26 | H | —CH=CH—Ph | H | —COOMe | CN | — | |
| 2-27 | H | —CH=CH—Ph | H | CN | CN | — | |
| 2-28 | H | 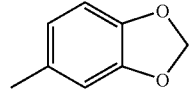 | Me | —COOMe | CN | — | |
| 2-29 | Me | 4-Cl—Ph | H | —COOEt | NO$_2$ | TRANS | $n_D^{22.5}$ 1.6342 |
| 2-30 | Me | 4-Cl—Ph | H | —COOEt | NO$_2$ | CIS | $n_D^{23}$ 1.6339 |
| 2-31 | Me | 4-Cl—Ph | H | —COOEt | NO$_2$ | CIS | [203–205] DEC |
| 2-32 | Me | 4-Cl—Ph | H | H | NO$_2$ | TRANS | [148–150] |
| 2-33 | Me | 4-Cl—Ph | H | H | NO$_2$ | CIS | [199–201] |
| 2-34 | Me | 4-Cl—Ph | H | —COOEt | CN | CIS | [121–123] |
| 2-35 | Me | 4-Cl—Ph | H | CN | CN | | |
| 2-36 | Me | 4-Cl—Ph | H | —COOEt | CN | TRANS | [228–231] |
| 2-37 | Me | 4-Cl—Ph | —CONH-cHex | H | NO$_2$ | CIS | [154–157] |
| 2-38 | Me | 4-Cl—Ph | —CONH-2-THP | H | NO$_2$ | | |
| 2-39 | Me | 4-Cl—Ph | —CONH-2-THP | —COOEt | CN | | |
| 2-40 | Me | 4-Cl—Ph | H | —SO$_2$-(4-Me—Ph) | CN | | |
| 2-41 | Me | 4-Cl—Ph | Et | —COOEt | CN | TRANS | [108–111] |
| 2-42 | Me | 4-Cl—Ph | Allyl | —COOEt | CN | CIS | Oily substance |
| 2-43 | Me | 4-Cl—Ph | —CH$_2$C≡CH | —COOEt | CN | TRANS | $n_D^{23}$ 1.6003 |
| 2-44 | Me | 4-Cl—Ph | Me | —COOEt | CN | | |
| 2-45 | Me | 4-Cl—Ph | —COEt | —COOEt | CN | TRANS | [168–170] |
| 2-46 | Me | 4-Cl—Ph | —SO$_2$Me | —COOEt | CN | TRANS | [210] |
| 2-47 | Me | 4-Cl—Ph | —SO$_2$Me | —COOEt | CN | CIS | [209–212] |
| 2-48 | Me | 4-Cl—Ph | Me | —COOEt | —COOEt | | |
| 2-49 | Me | 4-Cl—Ph | Bn | —COOEt | CN | TRANS | Oily substance |
| 2-50 | Me | 4-Cl—Ph | Bn | —COOEt | CN | CIS | $n_D^{34.5}$ 1.5627 |
| 2-51 | Me | 4-Cl—Ph | —COCH$_2$Cl | —COOEt | CN | TRANS | [175–177] |
| 2-52 | Me | 4-Cl—Ph | —COCH$_2$Cl | —COOEt | CN | CIS | [112–115] |
| 2-53 | Me | 4-Cl—Ph | —COOEt | —COOEt | CN | | $n_D^{20}$ 1.5690 |
| 2-54 | Me | 4-Cl—Ph | —CONH-cHex | —COOEt | CN | | |
| 2-55 | Me | 4-Me—Ph | —CH$_2$C≡CH | —COOEt | CN | | $n_D^{21.5}$ 1.5329 |
| 2-56 | Me | 4-Me—Ph | H | —COOEt | CN | | |
| 2-57 | Me | Bn | H | CN | CN | | |
| 2-58 | Me | —C$_2$H$_4$—Ph | H | —CONHMe | —CONHMe | | |
| 2-59 | Me | —CH=CH—Ph | H | —CONHMe | —CONHMe | | |
| 2-60 | Me | 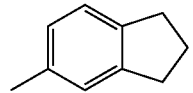 | H | —COOMe | CN | | |
| 2-61 | Me |  | H | —COOMe | CN | | |

TABLE 2-continued

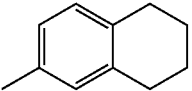

| Compound No. | R₁ | Q₁—R₂ | R₃ | R₄ | R₅ | R₁/Q₁—R₂ | PhysicalConstant [ ]:MeltingPoint °C. |
|---|---|---|---|---|---|---|---|
| 2-62 | Me | 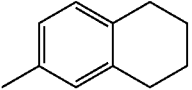 | H | —SO₂—Ph | CN | | |
| 2-63 | Me | (same) | H | —COOMe | CN | | |
| 2-64 | Me | 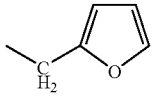 | Me | —COOMe | CN | | |
| 2-65 | Me | 4-Et—Ph | H | —COOMe | —COOMe | | |
| 2-66 | Me | Naph | H | —COOMe | —COOMe | | |
| 2-67 | Me | 4-Ph—Ph | Ac | —COOEt | CN | | |
| 2-68 | Me | 4-Me—Ph | —CO-Allyl | CN | CN | | |
| 2-69 | Me | 4-Me—Ph | —COOEt | CN | CN | | |
| 2-70 | Me | 4-Me—Ph | —CO-Pr-n | —SO₂-(4-MeO—Ph) | —SO₂—Ph | | |
| 2-71 | Me | 4-Me—Ph | —CONH-2-THP | CN | CN | | |
| 2-72 | Me | 4-Me—Ph | 4-MeO—Bz | CN | CN | | |
| 2-73 | Me | 4-Me—Ph | 3-MeSO₂—Bz | CN | CN | | |
| 2-74 | Me | 4-Me—Ph | Bz | CN | CN | | |
| 2-75 | Me | 4-Me—Ph | —SO₂Ph | —COOEt | CN | | |
| 2-76 | Me | 4-Me—Ph | —CONH-cHex | —COOEt | NO₂ | | |
| 2-77 | Me | 4-Me—Ph | —CONH-cHep | —COOEt | CN | | |
| 2-78 | Me | 4-Me—Ph | —CON(—Me)-cHex | —COOEt | NO₂ | | |
| 2-79 | Me | 4-Me—Ph | —CONH-(3-MeO-cHex) | —COOEt | NO₂ | | |
| 2-80 | Me | 4-Me—Ph | —CSNH-cHex | CN | CN | | |
| 2-81 | Me | 4-Me—Ph | —CONH-2-THP | —SO₂—Ph | NO₂ | | |
| 2-82 | Me | 4-Me—Ph | —CONH-2-Py | —SO₂—Ph | NO₂ | | |
| 2-83 | Me | 4-Me—Ph | —SO₂NMe₂ | —COOEt | NO₂ | | |
| 2-84 | Me | 4-Me—Ph | —CONHCO-cHex | —COOEt | NO₂ | | |
| 2-85 | Me | 4-Me—Ph | H | —COAllyl | COAllyl | | |
| 2-86 | Me | 4-CF₃—Ph | Ac | —COOEt | CN | | |
| 2-87 | Me | 4-(4-Me—Ph)—Ph | H | —COOEt | CN | | |
| 2-88 | Me | 4-Ph—O—Ph | H | —COOEt | CN | | |
| 2-89 | Me | 4-Ph—S—Ph | H | —COOEt | CN | | |
| 2-90 | Me | 4-Ac—Ph | Bz | —COOEt | NO₂ | | |
| 2-91 | Me | 4-AcO—Ph | H | —COOEt | NO₂ | | |
| 2-92 | Me | 4-MeOCO—Ph | H | —COOEt | NO₂ | | |
| 2-93 | Me | 4-MeSO₂—Ph | H | —SO₂-(4-AcO—Ph) | NO₂ | | |
| 2-94 | Me | 4-Br—Ph | H | —SO₂-(4-Cl—Ph) | NO₂ | | |
| 2-95 | Me | 4-n-Pr—Ph | H | —COOEt | NO₂ | | |
| 2-96 | Me | 4-CH₂Cl—Ph | 3-MeOCH₂O-Bn | —COOEt | NO₂ | | |
| 2-97 | Me | 4-CF₃CO—Ph | H | —COOEt | NO₂ | | |
| 2-98 | Me | 4-Allyl-Ph | H | —COOEt | NO₂ | | |
| 2-99 | Me | 4-Me—Ph | —CONH—CH₂COOMe | —COOMe | NO₂ | | |
| 2-100 | Et | 4-Cl—Ph | H | —COOEt | NO₂ | | |
| 2-101 | Et | 4-Me—Ph | H | —COOEt | —COMe | | |
| 2-102 | CF3 | 4-Me—Ph | H | —SO₂—Ph | CN | | |
| 2-103 | CH₂F | Ph | H | —COOEt | —COOEt | | |
| 2-104 | CH₂Cl | 4-Cl—Ph | H | —SO₂—Ph | —COOEt | | |
| 2-105 | C₂H₄Cl | 4-Cl—Ph | H | —SO₂—Ph | —COOEt | | |
| 2-106 | Ph | 4-PhO—Ph | H | —COOEt | —COOEt | | |
| 2-107 | 4-Me—Ph | 4-Me—Ph | H | —COOEt | —COOEt | | |
| 2-108 | Bn | Ph | H | —SO₂—Ph | CN | | |

TABLE 2-continued

[Structure: thiazolidine-like ring with R1, R3 on N, R2-Q1 on carbon, R4/R5 on exocyclic double bond]

| Compound No. | $R_1$ | $Q_1$—$R_2$ | $R_3$ | $R_4$ | $R_5$ | $R_1$/$Q_1$—$R_2$ | PhysicalConstant [ ]:MeltingPoint ° C. |
|---|---|---|---|---|---|---|---|
| 2-109 | Me | 4-Me—Ph | CONH—(tetrahydrofuran-2-yl) | CN | CN | | |
| 2-110 | Me | Ph | —CONH—(tetrahydrothiophen-2-yl) | —COOMe | CN | | |
| 2-111 | Me | 4-Me—Ph | —CONH—(tetrahydrofuran-2-yl) | —COOEt | $NO_2$ | | |
| 2-112 | Me | Ph | —CONH—(tetrahydrothiophen-2-yl) | —COOEt | —COOEt | | |
| 2-113 | Me | 4-Me—Ph | Me | —CONHMe | —CONHMe | | |
| 2-114 | Me | —$C_2H_4$—Ph | H | —$SO_2$—Ph | CN | | |
| 2-115 | Me | —CH═CH—Ph | H | —$SO_2$—Ph | $NO_2$ | | |

Next, the pharmaceutical formulation examples in the present invention are presented.

Pharmaceutical Formulation Example 1: Tablets

| Compositions | Amount (g) |
|---|---|
| Compound of the present invention | 5 |
| Lactose (The Pharmacopoeia of Japan) | 50 |
| Corn starch (The Pharmacopoeia of Japan) | 25 |
| Crystalline cellulose (The Pharmacopoeia of Japan) | 25 |
| Methyl cellulose (The Pharmacopoeia of Japan) | 1.5 |
| Magnesium stearate | 1 |

(The Pharmacopoeia of Japan)

A compound of the present invention, lactose, corn starch and crystalline cellulose were incorporated thoroughly. The mixture was formed into the granules with 5% aqueous solution of methyl cellulose, and the granules were passed through a sieve of 300 mesh and then dried carefully. The dried granules were incorporated with magnesium stearate and then prepared into tablets according to the conventional method to obtain 1,000 tablets.

Pharmaceutical Formulation Example 2: Capsules

| Compositions | Amount (g) |
|---|---|
| Compound of the present invention | 10 |
| Lactose (The Pharmacopoeia of Japan) | 80 |
| Starch (The Pharmacopoeia of Japan) | 30 |
| Talc (The Pharmacopoeia of Japan) | 5 |
| Magnesium stearate | 1 |

(The Pharmacopoeia of Japan)

The compositions recited above were incorporated and crushed into fine particulates. The particulates of the mixture were then stirred thoroughly so as to obtain the homogenous mixture. The mixture was then charged into capsules made of gelatin for oral administration use to obtain 1,000 pieces of two-pieces type gelatin capsules.

Pharmaceutical Formulation Example 3: Solution for Injection

| Compositions | Amount (g) |
|---|---|
| Compound of the present invention | 1 |
| Polyethylene glycol 4000 (The Pharmacopoeia of Japan) | 0.3 |
| Sodium chloride (The Pharmacopoeia of Japan) | 0.9 |
| Polyoxyethylene sorbitan monooleate (The Pharmacopoeia of Japan) | 0.4 |
| Sodium metabisulfite (The Pharmacopoeia of Japan) | 0.1 |
| Methylparaben (The Pharmacopoeia of Japan) | 0.18 |
| Propylparaben (The Pharmacopoeia of Japan) | 0.02 |
| Distilled water for injection use (Final volume) | Appropriate 100 (ml) |

The Parabens, sodium metabisulfite and sodium chloride were dissolved with approximately half of the final volume of distilled water for injection use at 80° C. while stirring. Then, the obtained solution was cooled down to 40° C. The compound of the present invention, and subsequently polyethylene glycol and polyoxyethylene sorbitan monooleate were added to the solution and dissolve therewith. Next, the rest portion of the distilled water was added into the solution so as to adjust the volume to the final volume mentioned. The solution was then filtered through an appropriate filter to sterilize to obtain the pharmaceutical formulation of aqueous solution suitable for parenteral use.

Pharmaceutical formulation Example 4: Ointment

| Compositions | Amount (g) |
| --- | --- |
| Compound of the present invention | 0.1 |
| White soft paraffin | 10 |

The compound of the present invention was incorporated into the base material so as to be homogeneous therein.

Pharmaceutical formulation Example 5: Aerosol

| Compositions | Amount (g) |
| --- | --- |
| Compound of the present invention | 0.25 |
| Ethanol | 29.75 |
| Propelant 22(Chlorodifluoromethane) | 70 |

The compound of the present invention was incorporated into ethanol and then added with 1 part of Propelant 22 to obtain a mixture. The mixture was then cooled down to −30° C. and then placed in a charging apparatus. Next, an amount of the mixture required for a administration was transferred into a stainless container and was diluted with the rest portion of the Propelant 22 to prepare the solution for a erosol. The stainless container was then mounted with a valve unit to be ready for the administration.

Pharmaceutical Formulation Example 6: Dry Powder for Inhalation

| Compositions | Amount (g) |
| --- | --- |
| Compound of the present invention | 5 |
| Lactose | 95 |

The compound of the present invention was mixed with lactose to obtain a homogeneous mixture. The mixture was then charged into an inhaler for dry powder.

Pharmaceutical Formulation Example 7: Suppositories

| Compositions | Amount (g) |
| --- | --- |
| Compound of the present invention | 0.225 |
| Saturated fatty acid glyceride | 2.000 |

The compound of the present invention was passed through No. 60 mesh U.S. sieve and then suspended in saturated fatty acid glyceride having been melted beforehand with minimum heat. The mixture was charged into a molding for suppositories with the indication capacity of 2 g and then cooled.

Industrial Use

Pharmacological Test Example 1:

PLA(2) Activity

The PLA(2) activity was measured by quantitatively analyzing the fluorescent product of hydrolysis from 1,2-bis-(4,4-difluoro-5,7-dimethyl-4-bora-3a,4a-diaza-s-indecene-3-undecanoyl)-sn-glycero-3-phosphocholine (hereinafter referred to bis-BODIPY®FL $C_{11}$-PC, Molecular probes, Inc., B-7701) using activated U937 cells (human monoblastic lymphoma cell line) by inflammatory stimulus (Meshulam, T. et al., *The journal of Biological Chemistry* 267 (30): 21465–21470 (1992); and Solito, E. et al., *British Journal of Pharmacology* 124: 1675–1683(1998).). The substrate bis-BODIPY®FL $C_{11}$-PC is incorporated into cellular membranes, the proximity of the BODIPY®FL fluorophores on adjacent phospholipid acyl chains causes fluorescence self-quenching. Separation of the fluorophores upon hydrolytic cleavage of one of the acyl chains by PLA(1) or the PLA(2) results in increased fluorescence. In the activated U937 cells by inflammatory stimuli, it is shown that this substrate should be cleaved enzymatically by IV-cPLA(2) from the feature of its behaviors including sensitivity profiles against the inhibitors.

The human cell line U937 was purchased from Dai-Nippon Pharmaceuticals Co., Ltd. The cells were maintained by transferring every 3–4 days into RPMI 1640 medium (Sigma Chemical Co., R6504) supplemented with heat-inactivated 10% fetal bovine serum (Fetal Bovine Serum, Sigma Chemical Co., F 4135) in a 5% $CO_2$ humidified atmosphere at 37° C. The cells were transferred into the culture medium described above, containing 1.2% (v/v) dimethylsulfoxide (hereinafter referred to as DMDO, Nacalai tesque Co., Ltd., D 134–45), and pre-cultured for 96 to 120 hours so as to differentiate into the macrophage-like cells to be provided for the assay. The macrophage-like cells were collected and washed by centrifugation with the Assay medium (Dulbecco's phosphate buffered saline (hereinafter referred to as PBS)-2.2 mM glucose-2.5 μM albumin). Then, Phorbol 12-Myristate 13-Acetate (hereinafter referred to as TPA, Sigma Chemical Co., P 8139) was added to the Assay medium to be $1 \times 10^{-8}$ M as the final concentration. Then, the macrophage-like cells were further cultured for an hour to be activated (Rzigalinski, B. A. & Rosenthal, M. D., *Biochimica et Biophysica Acta* 1223: 219–225 (1994); and Gonchar, M. V. et al., *Biochemical and Biophysical Research Communication*, 249: 829–832 (1998).).

For preparing substrate liposome suspension, bis-BODIPY®FL $C_{11}$-PC was combined with phosphatidylserine (Sigma Chemical Co., P7769) at 1:9 molar ratio in chloroform, and dried under nitrogen flow. The dried mixture was suspended with the Assay medium at 100 μg/mL, voltexed and sonicated for an hour on ice under dark condition.

The test compound was dissolved with DMSO at 30 mM, and the solution diluted with either DMSO or the Assay medium before addition into the reaction mixture. The DMSO concentration in the reaction mixture was controlled so as to be no more than 0.1%. The 30-fold concentration of test compound solution was put into each well of 96-Wells Microplate, (Falcon, 3072) at a rate of 2.5 μL/well. To the respective well was added 25 μL/well of the activated U937 cell suspension ($6 \times 10^6$ cells/mL), and the cells were pre-cultured for 120 min. at 37° C. in a 5% $CO_2$ atmosphere incubator. 47.5 µL/well of the substrate liposome suspension with $1.5\times10^{-6}$ M A23187 (Sigma Chemical Co., C 7522) was added into each well to prepare 75 µL/well of the total reaction mixture, followed by culture for 30 min. under the same conditions with shielding against light. 100 µL/well of 0.1% GEDTA (Dojindo Laboratories Co. Ltd., 348-01311) methanol solution was added into each well and mixed to stop the reaction. The increased fluorescence of the hydrolysis product by the enzyme was determined by measuring the fluorescence emission intensity at 535 nm with excitation at 485 nm from the top side of each plate at 37° C., using a Multi Functional Microplate Reader SPECTRA FLUOR PLUS (TECAN Austria GmbH). The measurements for the same test lot were carried out under the same sensitivity as the optimum gain condition for the first microplate measurement. In the test, each treatment was repeated three times, the reaction mixture plot without cells was used as the blank, and arachidonyl trifluoromethyl ketone (hereinafter referred to as $AACOCF_3$, Calbiochem-Novabiochem Corp., 100109) was used for the positive control treatment. PLA(2) activity in each test plot was determined by subtracting the mean value of the fluorescence emission intensity in the blank plot from that of each well, respectively. There was statistically no significant difference between the plots with and without 0.1% DMSO. In the pre-examination, the fluorescence emission intensity based on the substrate hydrolysis was increased linearly with time progression until 90 min. Besides, hydrolysis as the basic metabolic activity, which was measured as the enzymatic activity in the sub-cultured cells neither being differentiated nor activated, without A23187 treatment condition, was shown about one seventh of that exerted by the activated cells. Thus, the difference obtained by subtracting the basic metabolic activity from each enzymatic activity was determined as the inflammatory activated PLA(2) activity, and the inhibition rate was calculated by the inflammatory activated PLA(2) activity per the mean value of that of the control plots with and without DMSO, for evaluating the activity of the respective test compounds. The inhibitory activity measured for the respective compounds of the present invention are shown in Table 3 below, for example.

TABLE 3

| Compound No. | Concentration (µM) | Inhibition (%) |
| --- | --- | --- |
| 1-41 | 0.1 | 100 |
| 1-42 | 0.1 | 66 |
| 1-72 | 10 | 97 |
| 2-29 | 10 | 99 |
| 2-31 | 10 | 100 |
| 2-32 | 10 | 98 |
| 2-33 | 1 | 84 |
| 2-34 | 10 | 98 |
| 2-36 | 10 | 97 |
| 2-37 | 1 | 87 |
| 2-43 | 10 | 100 |
| 2-45 | 1 | 55 |
| 2-46 | 0.1 | 82 |
| 2-47 | 10 | 98 |
| 2-49 | 1 | 89 |
| 2-55 | 1 | 70 |
| $AACOCF_3$ | 3 | 65 |

Pharmacological Test Example 2:

Mouse Ear Edema Induced by TPA

This test was carried out referring to the method of Carlson, R. P. et al. (*Agents and Actions*, 17(2): 197–204 (1985).) and the method of Chang, J. (*European Journal of Pharmacology*, 142: 197–205 (1987).). More specifically, 5 µg/20 µL of TPA (Sigma Chemical Co.), dissolved with ethanol, was topically applied to the anterior and posterior surfaces of the right ear of an ICR-strain male mouse (6–7 weeks old). 6 hours later, the thickness of each ear at the particular part was respectively measured three times using a digimatic micrometer to calculate the mean value. Ear edema was determined by subtracting the mean thickness of the left ear as without treatment from that of the right ear as TPA-applied. Topical application activity was evaluated by applying an acetone solution of the compound of the present invention or 0.1% Tween 80/acetone solution thereof similarly to the anterior and posterior surfaces of the right ear 30 min. before and 15 min. after the TPA-application. As the positive control, an acetone solution of Dexamathasone-21-acetate (hereinafter referred to as DEX-Ac, Sigma Chemical Co., D 1881) and an acetone solution of indomethacin were applied similarly as for the compound of the present invention. Oral administration activity was evaluated by administrating 0.2% Tween 80 suspension of the compound of the present invention forcibly and perorally to the mouse an hour prior to the TPA-application. As the positive control, 100 mg/kg of Hydrocortisone (Sigma Chemical Co., H 4001) suspension was applied to the mouse similarly as for the compound of the present invention. By the treatment with the compounds of the present invention, anti-inflammatory activities, for example as shown in Table 4, were measured for the respective compounds. Furthermore, it was noted that the mice of both DEX-Ac administration group and indomethacin administration group showed intoxicated symptoms and their body weight were reduced after 24 hours. On the contrary, neither remarkable intoxicated symptom, nor significant change in their body weight was observed in the mice in the each group applied with the compounds of the present invention.

TABLE 4

| Compound No. | Dose (mg/µL/ear × 2) | Ear Edema Inhibition (%) |
| --- | --- | --- |
| 1-41 | 1 mg/40 µL | 80.5 |
| 2-29 | 0.3 mg/20 µL | 78.6 |
| 2-37 | 1 mg/40 µL | 35.2 |
| 2-43 | 0.3 mg/20 µL | 75.4 |
| 2-49 | 1 mg/40 µL | 65.9 |
| DEX-Ac | 1 mg/20 µL | 79.6 |
| Indomethacin | 3 mg/40 µL | 63.5 |

Pharmacological Test Example 3

Mouse Delayed Contact Dermatitis Induced by Picryl Chloride

This pharmacological test was carried out referring to the method of Asherson, G. L. & Ptak, W. (*Immunology*, 15: 405–416 (1968).) and the method of Jun Hiroi (*Folia Pharmacology of Japan*, 86: 233–239 (1985).). More specifically, hairs on the abdomen of an ICR-strain male mouse were removed using an electric clipper and an electric shaver. Then, 0.1 mL of 7% ether solution of picryl chloride (Tokyo Kasei Kogyo Co., Ltd., C 0307) was applied onto the abdomen for sensitization. On the sixth day after the sensitization, 20 µL/ear of 1% olive oil solution of picryl chloride was topically applied to the anterior and posterior surfaces of both ears of the mouse to induce contact dermatitis (first induction). Before and 24 hours after the induction, the thicknesses of the particular parts on the both ears were measured three times, respectively, using a digimatic micrometer (Mitsutoyo Co., Ltd.) to work out the average values. Ear edema of the both ears was respectively determined by subtracting the average thickness of the each ear before the induction from that on 24 hours after the induction, so that a grouping was carried out to separate the appropriate individuals. On the fourth day after the first induction, the hairs on the abdomen were removed again, and 0.1 mL of 7% ethanol solution of picryl chloride was applied thereto for additional sensitization. The contact dermatitis for evaluating activity was induced by re-applying 20 μL/ear of 1% olive oil solution of picryl chloride to the anterior and posterior surfaces of both ears (second induction) on the seventh day after the additional sensitization (on the 18th day after the first sensitization). The activity of each compound of the present invention was evaluated as the inhibition on the contact dermatitis as compared with that of the vehicle applied control. That is, the thicknesses of the particular portions of the both ears were measured respectively three times with a digimatic micrometer to work out the mean values before, 24 hours and 48 hours after the second induction. Ear swelling was determined by subtracting the ear thickness before the second induction from that on 24 hours and 48 hours after the second induction, respectively. Topical application activity was evaluated by applying 25 μL of the acetone solution of the compound of the present invention similarly to the anterior and posterior surfaces of the right ear one hour before and 16 hours after the second induction. As the positive control, 0.02 mg/20 μL of acetone solution of Dexamethasone (hereinafter referred to as DEX, Wako Pure Chemical Industries Ltd., 047-18863) was applied similarly as for the compound of the present invention. With respect to the inhibitory activity in topical application tests, the topical activity was determined by the inhibition of the applied right ear edema, and the translocation and distribution property was determined by the activity onto the swelling of non-treated left ear. Oral administration activity was evaluated by administrating 0.5% methyl cellulose suspension of the compound of the present invention forcibly and perorally to the mouse an hour before and 16 hours after the second induction. As the positive control, 20 mg/kg of Prednisolone (Sigma Chemical Co., P 6004) suspension was administrated similarly as for the compounds of the present invention. With respect to the compounds of the present invention, the anti-allergic activities as shown in Table 5 were measured. Furthermore, it was noted that the mice of DEX administrated group group showed intoxicated symptoms and their body weight were reduced significantly 48 hours after the second induction. On the contrary, neither remarkable intoxicated symptom, nor significant change in their body weight was observed in the mice in the each group applied with the compounds of the present invention. As the examples, the body weight changes in the mice for 48 hours after the second induction when they were administrated with the compounds shown in Table 5 are shown in Table 6.

TABLE 5

| Compound No. | Dose (mg/25 μL/ ear × 2) | Ear swelling after 24 hours | |
| --- | --- | --- | --- |
| | | Right (Applied) (Mean ± S.E., mm) | Left (Not applied) (Mean ± S.E., mm) |
| Vehicle Control | — | 0.299 ± 0.006 | 0.284 ± 0.008 |
| 2-29 | 1.5 | 0.261 ± 0.012 | 0.243 ± 0.020 |
| DEX | 0.02 | 0.057 ± 0.009 | −0.005 ± 0.033 |

TABLE 6

| Compound No. | Dose (mg/ ear × 2) | Body weight before induction (Mean ± S.E.) (g) | Change in body weight 48 hours after induction (Mean ± S.E.) | |
| --- | --- | --- | --- | --- |
| | | | (g) | (%) |
| Vehicle Control | — | 34.45 ± 0.85 | −0.45 ± 0.20 | −1.29 ± 0.59 |
| 2-29 | 1.5 | 31.52 ± 0.35 | −0.06 ± 0.15 | −0.20 ± 0.48 |
| DEX | 0.02 | 32.84 ± 0.73 | −1.42 ± 0.20 | −4.30 ± 0.59 |

Pharmacological Test Example 4:

Acetic Acid Wirthing

This test was carried out referring to the method of Inoue, K., Motonaga, A. & Nishimura, T (*Arzneimittel Forshung/Drug Research*, 41 (1): 235–239 (1991)). More specifically, 7.5 mL/kg of 0.9% acetic acid solution was injected intraperitoneally into an ICR-strain male mouse (5 to 7 weeks old), and the induced writhes (characteristic behaviors of convulsive contracting the abdomen, twisting the body and/or extending the legs) were observed. Number of writhes of each mouse was measured during 10 to 20 min. period after acetic acid administration. The compound of the present invention was homogeneously suspended in 2% Tween 80/saline for injection use, and was injected intraperitoneally 30 min. before the induction by the acetic acid injection. Alternatively, the compound of the present invention was homogeneously suspended in 2% Tween 80/distilled water, and was administrated orally two hours before the induction by the acetic acid injection. The analgesic activity of the compounds according to the present invention was evaluated on the basis of the degree of inhibiting the number writhes by the administration of the compounds. As the positive control, indomethacin or aspirin was administrated. The analgesic activity of the compounds according to the present invention measured in this test were exemplified in Table 7.

TABLE 7

| Compound No. | Application route | Dose (mg/kg) | Application time (min before) | Number of writhes (Mean ± S.E.) |
| --- | --- | --- | --- | --- |
| Vehicle Control | i.p. | — | 30 | 25.2 ± 2.2 |
| Vehicle Control | p.o. | — | 120 | 23.5 ± 3.1 |
| 1-41 | i.p. | 1 | 30 | 4.0 ± 1.9 |
| 1-41 | p.o. | 10 | 120 | 1.3 ± 0.8 |
| 2-29 | i.p. | 1 | 30 | 5.5 ± 1.9 |
| 2-29 | p.o. | 10 | 120 | 1.5 ± 0.7 |
| Indomethacin | i.p. | 10 | 30 | 4.8 ± 0.9 |
| Indomethacin | i.p. | 3 | 30 | 13.8 ± 3.0 |
| Indomethacin | p.o. | 3 | 60 | 6.8 ± 2.0 |
| Aspirin | i.p. | 30 | 30 | 9.5 ± 2.0 |
| Aspirin | p.o. | 100 | 60 | 9.5 ± 1.9 |

As it is understood from the results of the foregoing pharmacological tests, it is apparent that the compounds according to the present invention have excellent inhibitory activities on the PLA(2) activity, being less toxic, having strong anti-inflammatory activities and/or anti-allergic activities. Thus, the composites containing the compounds according to the present invention are useful as therapeutic and/or protective drugs of new type, since sick conditions accompanied the activated PLA(2) activity are cured to show excellent effects against such associated diseases, by the administration of the composites.

What is claimed is:
1. Compounds represented by a formula [I'] or pharmaceutically acceptable composites thereof;

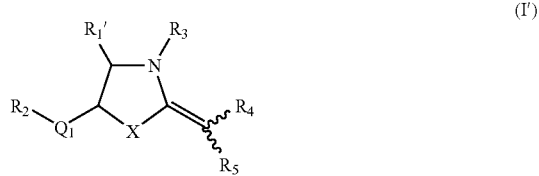

wherein X represents oxygen,
$Q_1$ represents —$(CH_2)_n$— or —CH=CH—,
n represents 0, or an integer ranging from 1 to 3,
$R_2$ represents optionally substituted by $A_1$, naphthyl optionall substituted by $A_1$, indanyl optionally substituted by $A_1$, or 1,2,3,4-tetrahydronaphthyl optionally substituted by $A_1$,
$R_3$ represents hydrogen, $C_{1-6}$ alkyl optionally substituted by $A_2$, $C_{2-6}$ alkenyl optionally substituted by $A_2$, $C_{2-6}$ alkynyl optionally substituted by $A_2$, $C_{1-6}$ alkylcarbonyl optionally substituted by $A_2$, $C_{2-6}$ alkenylcarbonyl optionally substituted by $A_2$, $C_{1-6}$ alkoxycarbonyl optionally substituted by $A_2$, $C_{2-6}$ alkenyloxycarbonyl optionally substituted by $A_2$, $C_{1-6}$ alkylsulfonyl optionally substituted by $A_2$, $C_{2-6}$ alkenylsulfonyl optionally substituted by $A_2$, benzoyl optionally substituted by $A_3$, phenylsulfonyl optionally substituted by $A_3$, or a group represented by the following formula:

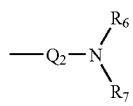

wherein $Q_2$ represents —CO—, —CS—, or —S(O)$_m$—,
$R_6$ represents hydrogen or $C_{1-6}$ alkyl,
$R_7$ represents $C_{1-6}$ alkyl optionally substituted by $A_2$, $C_{2-6}$ alkenyl optionally substituted by $A_2$, $C_{2-6}$ alkynyl optionally substituted by $A_2$, $C_{3-7}$ cycloalkyl optionally substituted by $A_4$, $C_{5-7}$ cycloalkenyl optionally substituted by $A_4$, $C_{1-6}$ alkylearbonyl optionally substituted by $A_2$, $C_{1-6}$ alkylsulfonyl optionally substituted by $A_2$, phenyl optionally substituted by $A_3$, benzoyl optionally substituted by $A_3$, or phenylsulfonyl optionally substituted by $A_3$,
m represents 1 or 2,
$R_4$ represents hydrogen, cyano, or a group represented by the following formula: -$Q_3$-$R_8$ wherein $Q_3$ represents —CO— or —S(O)$_m$—,
$R_8$ represents amino, $C_{1-6}$ alkyl optionally substituted by $A_2$, $C_{2-6}$ alkenyl optionally substituted by $A_2$, $C_{2-6}$ alkynyl optionally substituted by $A_2$, $C_{1-6}$ alkoxy optionally substituted by $A_2$, $C_{2-6}$ alkenyloxy optionally substituted by $A_2$, $C_{2-6}$ alkynyloxy optionally substituted by $A_2$, mono- or di-($C_{1-6}$ alkyl)amino optionally substituted by $A_2$, $C_{3-7}$ cycloalkyl optionally substituted by $A_4$, $C_{5-7}$ cycloalkenyl optionally substituted by $A_4$, phenyl optionally substituted by $A_3$, phenoxy optionally substituted by $A_3$, or anilino optionally substituted by $A_3$,
m represents 1 or 2,
$R_5$ represents nitro, cyano, or a group represented by the following formula: -$Q_3$-$R_8$ wherein $Q_3$ and $R_8$ are the same as defined above,
wherein $A_1$ represents halogen, nitro, cyano, $C_{1-6}$ alkyl, $C_{2-6}$ alkenyl, $C_{1-6}$ haloalkyl, $C_{3-7}$ cycloalkyl, phenyl $C_{1-6}$ alkoxy, methylenedioxy, $C_{1-6}$ alkylthio, $C_{1-6}$ alkylsulfenyl, $C_{1-6}$ alkylsulfonyl, mono- or di-($C_{1-6}$ alkyl) amino, $C_{1-6}$ haloalkoxy, benzyl, phenethyl, phenoxy, phenylthio, benzoyl, $C_{1-6}$ alkylcarbonyl, $C_{1-6}$ alkoxycarbonyl, $C_{1-6}$ haloalkylcarbonyl, $C_{1-6}$ haloalkoxycarbonyl, $C_{1-6}$ alkylcarbonyloxy, carbamoyl, or mono- or di-($C_{1-6}$ alkyl)carbamoyl, wherein phenyl is optionally substituted by halogen, $C_{1-6}$ alkyl or $C_{1-6}$ haloalkyl,
$A_2$ represents halogen, $C_{1-6}$ alkoxy, $C_{1-6}$ alkoxy $C_{1-6}$ alkoxy, amino, mono- or di-($C_{1-6}$ alkyl)amino, $C_{1-6}$ alkylcarbonyloxy, $C_{1-6}$ alkoxycarbonyl, mono- or di-($C_{1-6}$ alkyl)carbamoyl, mono- or di-($C_{1-6}$ alkyl)carbonylamino, morpholino, or phenyl,
$A_3$ represents halogen, hydroxy, oxo, mercapto, nitro, amino, cyano, $C_{1-6}$ alkyl, $C_{1-6}$ haloalkyl, $C_{1-6}$ alkoxy, $C_{1-6}$ alkylthio, $C_{1-6}$ alkylsulfenyl, $C_{1-6}$ alkylsulfonyl, mono- or di-($C_{1-6}$ alkyl)amino, $C_{1-6}$ haloalkoxy, $C_{1-6}$ alkylcarbonyl, $C_{1-6}$ alkoxycarbonyl, carbamoyl, mono- or di-($C_{1-6}$ alkyl)carbamoyl,
$A_4$ represents halogen, hydroxy, oxo, $C_{1-6}$ alkyl, $C_{1-6}$ haloalkyl, $C_{1-6}$ alkoxy, $C_{1-6}$ alkylthio, $C_{1-6}$ alkoxy $C_{1-6}$ alkoxy, $C_{1-6}$ alkylcarbonyl, $C_{1-6}$ alkylsulfonyl, or $C_{1-6}$ alkoxycarbonyl, and
$R_1'$ represents $C_{1-6}$ alkyl, $C_{1-6}$ haloalkyl, phenyl-$C_{1-6}$ alkyl wherein phenyl is optionally substituted by $A_1$, or phenyl optionally substituted by $A_1$,
with an exception of the following compounds, provisory:
X represents oxygen, $R_1'$ represents methyl, a group represented by $R_2$-$Q_1$ represents phenyl, $R_3$ represents hydrogen, both $R_4$ and $R_5$ represent cyano;
X represents oxygen, $R_1'$ represents methyl, a group represented by $R_2$-$Q_1$ represents phenyl, $R_4$ represents hydrogen, $R_5$ represents nitro.
2. A process for preparation, comprising reacting bismethylthioethylene compounds represented by the following formula (II):

wherein $R_5$ represents nitro, cyano, or a group represented by the following formula: -$Q_3$-$R_8$ wherein $Q_3$ represents —CO— or —S(O)$_m$—,
$R_8$ represents amino, $C_{1-6}$ alkyl optionally substituted by $A_2$, $C_{2-6}$ alkenyl optionally substituted by $A_2$, $C_{2-6}$ alkynyl optionally substituted by $A_2$, $C_{1-6}$ alkoxy optionally substituted by $A_2$, $C_{2-6}$ alkenyloxy optionally substituted by $A_2$, $C_{2-6}$ alkynyloxy optionally substituted by $A_2$, mono- or di-($C_{1-6}$ alkyl)amino optionally substituted by $A_2$, $C_{3-7}$ cycloalkyl optionally substituted by $A_4$, $C_{5-7}$ cycloalkenyl optionally substituted by $A_4$, phenyl optionally substituted by $A_3$, phenoxy optionally substituted by $A_3$, or anilino optionally substituted by $A_3$,
m represents 1 or 2,
$A_2$ represents halogen, $C_{1-6}$ alkoxy, $C_{1-6}$ alkoxy $C_{1-6}$ alkoxy, amino, mono- or di-($C_{1-6}$ alkyl)amino, $C_{1-6}$ alkylcarbonyloxy, $C_{1-6}$ alkoxycarbonyl, mono- or di-($C_{1-6}$ alkyl)carbamoyl, mono- or di-($C_{1-6}$ alkyl)carbonylamino, morpholino, or phenyl, $A_3$ represents halogen, hydroxy, oxo, mercapto, nitro, amino, cyano, $C_{1-6}$ alkyl, $C_{1-6}$ haloalkyl, $C_{1-6}$ alkoxy, $C_{1-6}$ alkylthio, $C_{1-6}$ alkylsulfenyl, $C_{1-6}$ alkylsulfonyl, mono- or di-($C_{1-6}$ alkyl)amino, $C_{1-6}$ haloalkoxy, $C_{1-6}$ alkylcarbonyl, $C_{1-6}$ alkoxycarbonyl, carbamoyl, mono- or di-($C_{1-6}$ alkyl)carbamoyl, $A_4$ represents halogen, hydroxy, oxo, $C_{1-6}$ alkyl, $C_{1-6}$ haloalkyl, $C_{1-6}$ alkoxy, $C_{1-6}$ alkylthio, $C_{1-6}$ alkoxy $C_{1-6}$ alkoxy, $C_{1-6}$ alkylearbonyl, $C_{1-6}$ alkylsulfonyl, or $C_{1-6}$ alkoxycarbonyl, and $R_4'$ represents cyano, or a group represented by the following formula: -$Q_3$-$R_8$ wherein $Q_3$ and $R_8$ are the same as defined above;

with 2-aminoethanol compounds represented by the following formula (III):

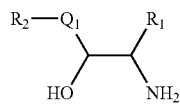

(III)

wherein $R_1$ represents hydrogen, $C_{1-6}$ alkyl, $C_{1-6}$ haloalkyl, phenyl-$C_{1-6}$ alkyl wherein phenyl is optionally substituted by $A_1$, or phenyl optionally substituted by $A_1$, $Q_1$ represents —(CH2)$_n$— or —CH=CH—, n represents 0, or an integer ranging from 1 to 3, $R_2$ represents phenyl optionally substituted by $A_1$, naphthyl optionally substituted by $A_1$, indanyl optionally substituted by $A_1$, or 1,2,3,4-tetrahydronaphthyl optionally substituted by $A_1$, wherein $A_1$ represents halogen, nitro, cyano, $C_{1-6}$ alkyl, $C_{2-6}$ alkenyl, $C_{1-6}$ haloalkyl, $C_{3-7}$ cycloalkyl, phenyl-$C_{1-6}$ alkoxy, methylenedioxy, $C_{1-6}$ alkylthio, $C_{1-6}$ alkylsulfenyl, $C_{1-6}$ alkylsulfonyl, mono- or di-($C_{1-6}$ alkyl)amino, $C_{1-6}$ haloalkoxy, benzyl, phenethyl, phenoxy, phenylthio, benzoyl, $C_{1-6}$ alkylcarbonyl, $C_{1-6}$ alkoxycarbonyl, $C_{1-6}$ haloalkylcarbonyl, $C_{1-6}$ haloalkoxycarbonyl, $C_{1-6}$ alkylcarbonyloxy, carbamoyl, or mono- or di-($C_{1-6}$ alkyl)carbamoyl, wherein phenyl is optionally substituted by halogen, $C_{1-6}$ alkyl or $C_{1-6}$ haloalkyl, and $A_4$ is as defined above, to obtain oxazolidine compounds represented by a formula (I-1):

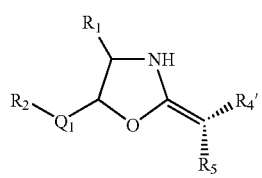

(I-1)

wherein $R_1$, $R_2$, $R_4'$, $R_5$, and $Q_1$ are the same as defined above.

3. A composition comprising as the active ingredient at least one compound selected from the group consisting of heterocyclic compounds represented by formula (I):

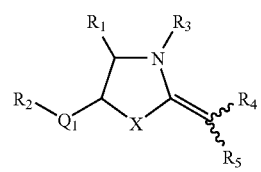

(I)

wherein X represents oxygen, $Q_1$ represents —(CH$_2$)$_n$— or —CH=CH—, n represents 0, or an integer ranging from 1 to 3, $R_1$ represents hydrogen, $C_{1-6}$ alkyl, $C_{1-6}$ haloalkyl, phenyl-$C_{1-6}$ alkyl wherein phenyl is optionally substituted by $A_1$, or phenyl optionally substituted by $A_1$, $R_2$ represents phenyl optionally substituted by $A_1$, naphthyl optionally substituted by $A_1$, indanyl optionally substituted by $A_1$, or 1,2,3,4-tetrahydronaphthyl optionally substituted by $A_1$, $R_3$ represents hydrogen, $C_{1-6}$ alkyl optionally substituted by $A_2$, $C_{2-6}$ alkenyl optionally substituted by $A_2$, $C_{2-6}$ alkynyl optionally substituted by $A_2$, $C_{1-6}$ alkylcarbonyl optionally substituted by $A_2$, $C_{2-6}$ alkenylcarbonyl optionally substituted by $A_2$, $C_{1-6}$ alkoxycarbonyl optionally substituted by $A_2$, $C_{2-6}$ alkenyloxycarbonyl optionally substituted by $A_2$, $C_{1-6}$ alkylsulfonyl optionally substituted by $A_2$, $C_{2-6}$ alkenylsulfonyl optionally substituted by $A_2$, benzoyl optionally substituted by $A_3$, phenylsulfonyl optionally substituted by $A_3$, or a group represented by the following formula:

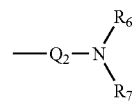

wherein $Q_2$ represents —CO—, —CS—, or —S(O)$_m$—, $R_6$ represents hydrogen or $C_{1-6}$ alkyl, $R_7$ represents $C_{1-6}$ alkyl optionally substituted by $A_2$, $C_{2-6}$ alkenyl optionally substituted by $A_2$, $C_{2-6}$ alkynyl optionally substituted by $A_2$, $C_{3-7}$ cycloalkyl optionally substituted by $A_4$, $C_{5-7}$ cycloalkenyl optionally substituted by $A_4$, $C_{1-6}$ alkylcarbonyl optionally substituted by $A_2$, $C_{1-6}$ alkylsulfonyl optionally substituted by $A_2$, phenyl optionally substituted by $A_3$, benzoyl optionally substituted by $A_3$, or phenylsulfonyl optionally substituted by $A_3$, m represents 1 or 2, $R_4$ represents hydrogen, cyano, or a group represented by the following formula: -$Q_3$-$R_8$ wherein $Q_3$ represents —CO— or —S(O)$_m$—, $R_8$ represents amino, $C_{1-6}$ alkyl optionally substituted by $A_2$, $C_{2-6}$ alkenyl optionally substituted by $A_2$, $C_{2-6}$ alkynyl optionally substituted by $A_2$, $C_{1-6}$ alkoxy optionally substituted by $A_2$, $C_{2-6}$ alkenyloxy optionally substituted by $A_2$, $C_{2-6}$ alkynyloxy optionally substituted by $A_2$, mono- or di-($C_{1-6}$ alkyl)amino optionally substituted by $A_2$, $C_{3-7}$ cycloalkyl optionally substituted by $A_4$, $C_{5-7}$ cycloalkenyl optionally substituted by $A_4$, phenyl optionally substituted by $A_3$, phenoxy optionally substituted by $A_3$, or anilino optionally substituted by $A_3$, m represents 1 or 2, $R_5$ represents nitro, cyano, or a group represented by the following formula: $-Q_3-R_8$ wherein $Q_3$ and $R_8$ are the same as defined above, $A_1$ represents halogen, nitro, cyano, $C_{1-6}$ alkyl, $C_{2-6}$ alkenyl, $C_{1-6}$ haloalkyl, $C_{3-7}$ cycloalkyl, phenyl-$C_{1-6}$ alkoxy, methylenedioxy, $C_{1-6}$ alkylthio, $C_{1-6}$ alkylsulfenyl, $C_{1-6}$ alkylsulfonyl, mono- or di-($C_{1-6}$ alkyl)amino, $C_{1-6}$ haloalkoxy, benzyl, phenethyl, phenoxy, phenylthio, benzoyl, $C_{1-6}$ alkylcarbonyl, $C_{1-6}$ alkoxycarbonyl, $C_{1-6}$ haloalkylcarbonyl, $C_{1-6}$ haloalkoxycarbonyl, $C_{1-6}$ alkylcarbonyloxy, carbamoyl, or mono- or di-($C_{1-6}$ alkyl)carbamoyl, wherein phenyl is optionally substituted by halogen, $C_{1-6}$ alkyl or $C_{1-6}$ haloalkyl, $A_2$ represents halogen, $C_{1-6}$ alkoxy, $C_{1-6}$ alkoxy $C_{1-6}$ alkoxy, amino, mono- or di-($C_{1-6}$ alkyl)amino, $C_{1-6}$ alkylcarbonyloxy, $C_{1-6}$ alkoxycarbonyl, mono- or di-($C_{1-6}$ alkyl)carbamoyl, mono- or di-($C_{1-6}$ alkyl)carbonylamino, morpholino, or phenyl, $A_3$ represents halogen, hydroxy, oxo, mercapto, nitro, amino, cyano, $C_{1-6}$ alkyl, $C_{1-6}$ haloalkyl, $C_{1-6}$ alkoxy, $C_{1-6}$ alkylthio, $C_{1-6}$ alkylsulfenyl, $C_{1-6}$ alkylsulfonyl, mono- or di-($C_{1-6}$ alkyl)amino, $C_{1-6}$ haloalkoxy, $C_{1-6}$ alkylcarbonyl, $C_{1-6}$ alkoxycarbonyl, carbamoyl, mono- or di-($C_{1-6}$ alkyl)carbamoyl, and $A_4$ represents halogen, hydroxy, oxo, $C_{1-6}$ alkyl, $C_{1-6}$ haloalkyl, $C_{1-6}$ alkoxy, $C_{1-6}$ alkylthio, $C_{1-6}$ alkoxy $C_{1-6}$ alkoxy, $C_{1-6}$ alkylcarbonyl, $C_{1-6}$ alkylsulfonyl, or $C_{1-6}$ alkoxycarbonyl, and pharmaceutically acceptable composites thereof.

* * * * *